United States Patent [19]
Temperante et al.

[11] Patent Number: 5,804,625
[45] Date of Patent: Sep. 8, 1998

[54] FLUOROCHEMICAL AND HYDROCARBON SURFACTANT BLENDS AS HYDROPHILIC ADDITIVES TO THERMOPLASTIC POLYMERS

[75] Inventors: John A. Temperante, St. Paul; Thomas P. Klun, Lakeland; Alton J. Gasper, Minneapolis, all of Minn.

[73] Assignee: Minnesota Mining and Manufacturing Company, St. Paul, Minn.

[21] Appl. No.: 646,791

[22] Filed: May 21, 1996

[51] Int. Cl.$^6$ .............................. C08K 5/54; C08K 5/20; C08K 5/36; C08K 5/48
[52] U.S. Cl. ................... 524/188; 524/220; 524/243; 524/265; 524/340
[58] Field of Search .................... 524/188, 220, 524/243, 265, 340

[56] References Cited

U.S. PATENT DOCUMENTS

| | | | |
|---|---|---|---|
| 2,723,999 | 11/1955 | Cowen et al. | 260/615 |
| 2,915,554 | 12/1959 | Ahlbrecht et al. | 260/556 |
| 3,489,148 | 1/1970 | Duncan et al. | 128/284 |
| 3,592,194 | 7/1971 | Duncan | 128/287 |
| 3,787,351 | 1/1974 | Olson | 260/40 R |
| 3,860,003 | 1/1975 | Buell | 128/284 |
| 3,870,567 | 3/1975 | Palmer et al. | 136/148 |
| 3,871,378 | 3/1975 | Duncan et al. | 128/290 |
| 4,324,246 | 4/1982 | Mullane et al. | 128/287 |
| 4,589,876 | 5/1986 | Van Tilburg | 604/385 |
| 4,857,251 | 8/1989 | Nohr et al. | 264/103 |
| 4,920,168 | 4/1990 | Nohr et al. | 524/188 |
| 4,923,914 | 5/1990 | Nohr et al. | 524/99 |
| 4,933,229 | 6/1990 | Insley et al. | 428/224 |
| 5,043,195 | 8/1991 | Skrivseth | 428/35.3 |
| 5,087,520 | 2/1992 | Suzuki et al. | 428/389 |
| 5,114,646 | 5/1992 | Nohr et al. | 264/103 |
| 5,120,888 | 6/1992 | Nohr et al. | 524/99 |
| 5,145,727 | 9/1992 | Potts et al. | 428/198 |
| 5,149,576 | 9/1992 | Potts et al. | 428/198 |
| 5,217,767 | 6/1993 | Gutman et al. | 428/35.3 |
| 5,244,951 | 9/1993 | Gardiner | 524/168 |
| 5,283,023 | 2/1994 | Nohr et al. | 264/103 |
| 5,300,357 | 4/1994 | Gardiner | 428/224 |
| 5,629,376 | 5/1997 | Sargent et al. | 524/745 |

FOREIGN PATENT DOCUMENTS

| | | | |
|---|---|---|---|
| 0 683 260 | 11/1995 | European Pat. Off. | D04H 1/42 |
| 1 337 467 | 11/1973 | United Kingdom | C09K 13/00 |
| 2 285 262 | 7/1995 | United Kingdom | C11D 1/825 |

OTHER PUBLICATIONS

Research Disclosure, Abstract 35324, p. 593 (Sep. 1993).
Wente, "Superfine Thermoplastic Fibers," *Industrial and Engineering Chemistry*, vol. 48, No. 8, pp. 1342–1346 (Aug., 1956).
Wente et al., "Manufacturing of Superfine Organic Fibers," Naval Research Laboratory Report No. 4364 (May 25, 1954).
U.S. Serial No. 07/438,593, now U.S. Pat. No. 5,501,679.

*Primary Examiner*—Kriellion S. Morgan
*Attorney, Agent, or Firm*—John A. Burtis

[57] ABSTRACT

This invention provides durably hydrophilic, thermoplastic fiber comprising a thermoplastic polymer, such as polyamide, polyurethane, or polyolefin, e.g., polypropylene, and a mixture of: (a) one or more fluoroaliphatic group-containing nonionic surfactants and (b) one or more nonionic, non-fluorinated, polyoxyethylene group-containing surfactants that contain between 20 and 80 weight percent polyoxyethylene. The mixture of the surfactants (a) and (b) is present in the fiber in an amount sufficient to impart durable hydrophilicity to the fiber at its surface. Durably hydrophilic films and durably hydrophilic fabrics and webs constructed from said fibers are also disclosed.

35 Claims, No Drawings

FLUOROCHEMICAL AND HYDROCARBON SURFACTANT BLENDS AS HYDROPHILIC ADDITIVES TO THERMOPLASTIC POLYMERS

FIELD OF THE INVENTION

This invention relates to fiber compositions comprising thermoplastic polymer, such as polypropylene. In another aspect, the present invention relates to methods of preparing durably hydrophilic fiber from normally hydrophobic thermoplastic polymer. In yet another aspect, it relates to fabrics comprising durably hydrophilic fiber, useful, for example, as liners for diapers, and to methods of making such fibers.

BACKGROUND OF THE INVENTION

Thermoplastic polymers are widely employed to create a variety of products, including blown and cascade films, extruded sheets, foams, fibers and products made therefrom, woven and knitted fabrics, and non-woven fibrous webs. Many thermoplastic polymers used in these products, such as polypropylene, are inherently hydrophobic, and there are a number uses for thermoplastic polymers where their hydrophobic nature either limits their use or requires some effort to modify the surface of the shaped articles made therefrom. For example, polyolefins are used in the manufacture of nonwoven webs that are employed in the construction of absorbent articles such as diapers, feminine care products, and personal incontinence products, the use of such articles self-evidently are limited because of their hydrophobic nature.

When fiber, and the fabrics made therefrom, is still hydrophilic after drying following contact with deionized water, the fiber or fabric is considered durably hydrophilic. Hydrophilic fiber is known to be obtained by topically spraying or coating the hydrophobic fiber with certain surfactants and subsequently drying the fiber or fabric. Typically, however, the surfactant that remains on the fiber using this technique is diminished or lost completely upon contact with an aqueous medium, e.g. water, and thus the hydrophilicity of the fibers is only poorly durable. Hydrophilicity, or the lack thereof, can be measured in a variety of ways. For example, when water contacts a nonwoven web that has lost its hydrophilicity, the water does not flow, or flows undesirably slowly, through the web.

Certain classes of hydrocarbon, silicone, and fluorochemical surfactants have each been described as useful for imparting hydrophilicity to polyolefins. These surfactants typically are contacted with the thermoplastic resin in one of two ways: (1) by topical application, e.g., spraying or padding or foaming, of the surfactants from aqueous solution to the extruded nonwoven web followed by drying, or (2) by incorporation of the surfactant into the polyolefin melt prior to extrusion of the web. As previously described, webs made hydrophilic by topical application of a surfactant suffer diminished hydrophilicity after a single contact with aqueous media, thus webs treated in this manner are considered non-durably hydrophilic. Additional disadvantages to topical application of a surfactant to impart hydrophilicity include skin irritation from the surfactant itself, non-uniform surface and bulk hydrophilicity, and the additive cost resulting from the necessity of an added processing step in the surfactant application. Incorporating one or more surfactants into to the thermoplastic polymer as a melt additive alleviate the problems associated with topical application and in addition may provide a softer "hand" to the fabric or nonwoven web into which it is incorporated.

The topical application of a hydrophilicity-imparting agent to a thermoplastic polymer is taught, for example, by Great Britain Patent No. 1 337 467 which discloses an aqueous, topically applied composition comprising water, an organic surface active agent having as the hydrophobic portion of the molecule one or more linear or branched aliphatic hydrocarbon groups, and an organic surface active agent having as the hydrophobic portion of the molecule one or more linear or branched aliphatic fluorocarbon groups. An anonymous submission to RESEARCH DISCLOSURE, September 1993, Abstract 35324, at 593 discloses a hydrophilic finish for olefinic nonwovens which is applied by dipping the material repeatedly in water and alcohol to clean the surface, followed by dipping into organic solvent containing a low percentage of water insoluble, nonionic hydrocarbon material.

The addition of one or more surfactants to the melts of thermoplastic polymers to impart hydrophilicity to both the surface and the bulk of the fiber is also taught in the art. U.S. Pat. Nos. 4,857,251 and 4,920,168 (Nohr et al.) describe a method of forming fibers by melt-extrusion of a surface segregatable thermoplastic composition that comprises thermoplastic polymer and siloxane-containing additive having certain moieties. After the fiber is formed, it is heated from 27° C. to 95° C. for a period of time sufficient to increase the amount of additive at the fiber surface. The resulting fiber has increased surface hydrophilicity compared to fibers prepared from the thermoplastic alone.

U.S. Pat. No. 5,087,520 (Suzuki et al.) describes fibers useful as surface materials for paper, diapers, sanitary napkins, incontinence products, etc. comprising a polyolefin or polyester having a mixture of a fatty acid diethanolamide, a polyether-modified silicone, a sorbitan fatty acid ester and a metal salt of an alkylsulfonate.

U.S. Pat. Nos. 5,244,951 and 5,300,357 (Gardiner) describe durably hydrophilic, thermoplastic fibers and fabrics made therefrom, for example, liners for diapers, comprising thermoplastic polymer and a fluoroaliphatic group-containing non-ionic compound.

SUMMARY OF THE INVENTION

Briefly, in one aspect, this invention provides durably hydrophilic, thermoplastic fiber comprising a thermoplastic polymer, such as polyamide, polyurethane, or polyolefin, e.g., polypropylene, and a mixture of: (a) one or more fluoroaliphatic group-containing nonionic surfactants and (b) one or more nonionic, non-fluorinated, polyoxyethylene group-containing surfactants that contain between 20 and 80 weight percent polyoxyethylene. The mixture of the surfactants (a) and (b) is present in the fiber in an amount sufficient to impart durable hydrophilicity to the fiber at its surface.

In another aspect, the present invention provides durably hydrophilic films and durably hydrophilic fabrics and webs constructed from said fibers. The invention also provides useful articles made from durably hydrophilic fabrics and webs including medical drapes, filter media, industrial wipes and battery separators that comprise the fabric of the invention which functions as the aqueous media absorbent structure in the articles. In yet another aspect, this invention provides multi-layer, aqueous liquid-absorbent articles comprising an aqueous media impervious backing sheet, an aqueous media permeable topsheet, and an aqueous liquid-absorbent (i.e., hydrophilic) layer constructed of the above-described web or fabric juxtaposed therebetween useful, for instance, in constructing disposable diapers, wipes or towels, sanitary napkins, battery separators and incontinence pads.

This invention also provides a method of preparing durably hydrophilic fiber from a mixture or blend of thermoplastic film-forming polymer, fluoroaliphatic group-containing nonionic surfactant, and non-fluorinated, nonionic polyoxyethylene group-containing surfactant. The melt of the mixture or blend is processed or shaped, for example, by extrusion or molding to produce fibers with the surfactants dispersed within the fiber and present at the surfaces of the fiber to render those surfaces durably hydrophilic. Because some surfactants demonstrate thermal sensitivity, the processing temperatures in the extruder are preferably kept below about 310° C., more preferably below about 300° C., where those surfacants are exposed to such temperatures given the particular processing technique. The durable hydrophilicity is achieved without requiring post fiber-spinning operations, e.g. heating, because the fiber is durably hydrophilic as extruded.

The total hydrophilicity imparted to a thermoplastic fiber, fabric, or nonwoven web by the surfactant blends of this invention is synergistic, i.e., greater than the amount of hydrophilicity that would be predicted from the sum of the proportionate hydrophilic contributions from each surfactant alone.

Such synergy is very advantageous as the fluorochemical/non-fluorinated surfactant additive blend is far more economical to use than the fluorochemical surfactant alone.

DETAILED DESCRIPTION OF THE INVENTION

As used herein, the terms "fiber" and "fibrous" refer to particulate matter, generally thermoplastic resin, wherein the length to diameter ratio of the particulate matter is greater than or equal to about 10. Fiber diameters may range from about 0.5 micron up to at least 1,000 microns. Each fiber may have a variety of cross-sectional geometries, may be solid or hollow, and may be colored by, e.g., incorporating dye or pigment into the polymer melt prior to extrusion. The surfactant blends of this invention modify both the surface and the bulk of each fiber in a uniform way. Thus, if some surfactant is washed from the surface of the fibers, the surfactant reservoir within the fiber supplies more of each surfactant to the surface of the fiber and thus replenishes the fiber's hydrophilicity.

The term "nonwoven web" or "fabric" refers to a construction made by intermingling fibers immediately after extrusion where the construction represents a much higher surface area-to-volume ratio than would be realized if a film were extruded and is thus very useful for absorption purposes, particularly when the nonwoven web is made more hydrophilic. Hydrophilic nonwoven webs are useful, for instance, in making medical drapes, facial tissues, filter media, industrial wipes and battery separators. Aqueous media absorbent articles will frequently comprise an aqueous media-impervious backing sheet (e.g., polypropylene or polyethylene), an aqueous media-permeable (i.e., porous) top sheet, and an aqueous liquid-absorbent layer or core positioned between said backing and said top sheet, a construction useful, for instance, in disposable diapers, sanitary napkins, tampons, and incontinence pads. Hydrophilic thermoplastic polymers of this invention are useful to replace or supplement the wood pulp fiber web liquid-absorbent layer or core typically used in conventional diapers. The hydrophilic polymers of the invention may also be used to input hydrophilicity to the top sheet of such an article where hydrophilicity is desired. The nonwoven webs or fabrics of this invention are readily prepared by processes used in the manufacture of either melt-blown or spun-bonded webs. For example, a process similar to that described in Wente, *Superfine Thermoplastic Fibers,* 48 INDUS. ENG'G CHEM. 1342(1956), or in WENTE ET AL., *MANUFACTURE OF SUPERFINE ORGANIC FIBERS,* (Naval Research Laboratories Report No. 4364, 1954) can be used for the preparation of the nonwoven webs of this invention.

As used herein, "hydrophilicity" will refer to the ability to be wet by aqueous-based liquids, polar liquids (such as ethylene glycol), aqueous solutions (such as KOH and $H_2SO_4$), or any combination thereof Thermoplastic polymers useful in this invention are generally hydrophobic polymers and include fiber-forming polyolefins such as polypropylene, polyethylene, and polybutylene. Blends of one or more thermoplastic polymers are also considered useful. Other useful fiber-forming thermoplastic polymers include thermoplastic polyesters, polyurethanes, and polyamides. Especially preferred is polypropylene.

Fluorochemical and non-fluorochemical (i.e., hydrocarbon- and silicone-containing) surfactants useful for making the surfactant blends that impart hydrophilicity to thermoplastic nonwoven webs and their aggregate fibers are all nonionic in type, (i.e., have no ionic charge in the molecule) and all contain polyoxyalkylene water-solubilizing groups in their chemical structures.

Particularly useful fluorochemical surfactants include fluoroaliphatic group-containing nonionic compounds that contain one or more blocks of water-solubilizing polyoxyalkylene groups in their structures. A class of such surfactants is described in U.S. Pat. No. 5,300,357 (Gardiner), whose descriptions are incorporated herein by reference. Generally, the fluorochemical surfactants useful in the invention include those represented below by Formula I.

$$(R_f\text{—}Q)_n\text{—}Z \tag{I}$$

wherein:

$R_f$ is a fluoroaliphatic group having at least 4 fully-fluorinated carbon atoms that may be straight-chained, branched, or, if sufficiently large, cyclic, or any combination thereof. The skeletal chain in the fluoroaliphatic radical can include one or more catenary heteroatoms, such as oxygen, hexavalent sulfur, and trivalent nitrogen atoms bonded only to carbon atoms of the skeletal chain. Fully fluorinated fluoroaliphatic groups are preferred, but hydrogen or chlorine atoms may be present as substituents provided that not more than one atom of either if present for every two carbon atoms. While $R_f$ can contain a large number of carbon atoms, compounds where $R_f$ is not more than 20 carbon atoms will be adequate and preferred since larger radicals usually represent a less efficient utilization of the fluorine than is possible with shorter chains. Fluoroaliphatic radicals containing from about 6 to about 12 carbon atoms are most preferred. Generally, $R_f$ will contain between about 40 and about 78 weight percent fluorine. The terminal portion of the $R_f$ group preferably contains at least four fully fluorinated carbon atoms, e.g., $CF_3CF_2CF_2CF_2$—, and particularly preferred compounds are those in which the $R_f$ group is fully or substantially completely fluorinated, as in the case where $R_f$ is a perfluoroalkyl, e.g., $CF_3(CF_2)_n$—. Suitable $R_f$ groups include, for example, $C_8F_{17}$—, $C_6F_{13}CH_2CH_2$—, and $C_{10}F_{21}$—$CH_2CH_2$—.

Q in Formula I above is a multivalent, generally divalent, linking group, or is a covalent bond, that provides a means to link $R_f$ with the depicted group Z, which is a nonionic, water-solubilizing group; Q can comprise a heteroatom-containing group, e.g., a group such as —S—, —O—, —CO—, —SO$_2$—, —N(R)—(where R is a hydrogen or a C$_1$ to C$_6$ substituted or unsubstituted alkyl group that may comprise a catenary heteroatom such as O, N, S), —C$_n$H$_{2n}$—(n=1 to 6); Q can comprise a combination of such groups such as would give, for example, —CON(R)C$_n$H$_{2n}$—, —SO$_2$N(R)C$_n$H$_{2n}$—, —SO$_3$C$_6$H$_4$N(R)C$_n$H$_{2n}$—, —SO$_2$N(R)C$_n$H$_{2n}$O [CH$_2$CH(CH$_2$Cl)O]$_g$CH$_2$CH(CH$_2$Cl)—(n=1 to 6; g=1 to 10), —SO$_2$N(CH$_3$)C$_2$H$_4$OCH$_2$CH(OH)CH$_2$—, —SO$_2$N(C$_2$H$_5$)C$_2$H$_4$OCH$_2$CH(OH)CH$_2$—, —SO$_2$N(H)CH$_2$CH(OH)CH$_2$NHC(CH$_3$)CH$_2$—, —(CH$_2$)$_2$S(CH$_2$)$_2$—, and —(CH$_2$)$_4$SCH(CH$_3$)CH$_2$—;

Z in Formula I above is a nonionic, water-solubilizing group comprising a poly(oxyalkylene) group, (OR')$_x$, where R' is an alkylene group having from 2 to about 4 carbon atoms, such as —CH$_2$CH$_2$—, —CH$_2$CH$_2$CH$_2$—, —CH(CH$_3$)CH$_2$—, and —CH(CH$_3$)CH(CH$_3$)—, and x is a number between about 6 and about 20; Z preferably contains a poly(oxyethylene) group. The oxyalkylene units in said poly(oxyalkylene) being the same, such as in poly(oxypropylene), or present as a mixture, such as in a heteric straight or branched chain of randomly distributed oxyethylene and oxypropylene units i.e., poly(oxyethylene-co-oxypropylene), or as in a straight or branched chain blocks of oxypropylene units. The poly(oxyalkylene) chain can be interrupted by or include one or more catenary linkages such as where Z includes a group of the formula —O—CH$_2$—CH(O—)—CH$_2$—O—, providing such linkages do not substantially alter the water-solubilizing character of the poly(oxyalkylene) chain. The Z group may be terminated with a hydroxyl, lower alkyl ether, alkaryl ether, or fluoroalkyl ether, for example, —OCH$_3$, —OCH$_2$CH$_3$, —OC$_6$H$_4$C(CH$_3$)$_2$CH$_2$C(CH$_3$)$_2$CH$_3$, —OC$_6$H$_4$(C$_9$H$_{19}$)$_2$, —OC$_{12}$H$_{25}$, —OC$_{14}$H$_{29}$, —OC$_{16}$H$_{33}$, or —O—QR$_f$(where Q and R$_f$ are as defined supra); and n is a number from 1 to 6.

Fluoroaliphatic group-containing nonionic surfactants, including those depicted supra by Formula I, may be prepared using known methods including those methods described in U.S. Pat. No. 2,915,554 (Albrecht et al.). The Albrecht patent discloses the preparation of fluoroaliphatic group-containing nonionic compounds from active hydrogen-containing fluorochemical intermediates, such as fluoroaliphatic alcohols (e.g., R$_f$C$_2$H$_4$OH), acids (e.g., R$_f$SO$_2$N(R)CH$_2$CO$_2$H), and sulfonamides (e.g., R$_f$SO$_2$N(R)H) by reaction of the intermediates with, for example, ethylene oxide to yield, respectively, R$_f$C$_2$H$_4$(OC$_2$H$_4$)$_n$OH, R$_f$SO$_2$N(R)CH$_2$CO$_2$(C$_2$H$_4$O)$_n$H, and R$_f$SO$_2$N(R)(C$_2$H$_4$O)$_n$H, where n is a number greater than about 3 and R is a hydrogen or a lower alkyl group (e.g., from 1 to 6 carbon atoms). Analogous compounds may be prepared by treating the intermediate with propylene oxide. The fluoroaliphatic oligomers disclosed in U.S. Pat. No. 3,787,351 (Olson), and certain fluorinated alcohol-ethylene oxide condensates described in U.S. Pat. No. 2,723,999 (Cowen et al.), whose descriptions are incorporated herein by reference, are also considered useful. Fluoroaliphatic group-containing nonionic surfactants containing hydrophobic longchain hydrocarbon groups may be prepared by reacting a fluoroaliphatic epoxide, such as

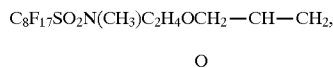

with, for example, an ethoxylated alkylphenol or alcohol, such as CH$_3$C(CH$_3$)$_2$CH$_2$C(CH$_3$)$_2$C$_6$H$_4$(OC$_2$H$_4$)$_{9.5}$OH or C$_{12}$H$_{25}$(OC$_2$H$_4$)$_9$OH, respectively in the presence of BF$_3$ etherate. They may also be prepared by first converting the ethoxylated alkylphenol or alcohol to a chloride by reaction with thionyl chloride, then reacting the resulting chloride with a fluoroaliphatic sulfonamide containing an active hydrogen, for example C$_8$F$_{17}$SO$_2$NH(CH$_3$), in the presence of sodium carbonate and potassium iodide.

One class of useful non-fluorinated, nonionic polyoxyethylene-containing surfactants for combination with the fluoroaliphatic surfactants described above include those that may be represented generally by the following formula:

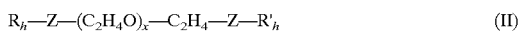

wherein:

R$_h$ is an alkyl or an aryl group, or in combination thereof, that may be substituted or unsubstituted and that contain from 2 to about 20 carbon atoms whose skeletal chain may be straight-chained, branched, or, if sufficiently large, cyclic, or any combination thereof, the skeletal chain can also optionally include one or more catenary heteroatoms such as oxygen, hexavalent sulfur, and trivalent nitrogen atoms bonded to the carbon atoms of the skeletal chain;

R'$_h$ is a hydrogen atom or is an alkyl or an aryl group, or in combination thereof, that may be substituted or unsubstituted and that contain from 2 to about 20 carbon atoms whose skeletal chain may be straight-chained, branched, or, if sufficiently large, cyclic, or any combination thereof; the skeletal chain can also optionally include one or more catenary heteroatoms such as oxygen, hexavalent sulfur, and trivalent nitrogen atoms bonded to the carbon atoms of the skeletal chain;

one or both of the depicted R$_h$ and R'$_h$ may contain a polydialkylsiloxane group of the formula:

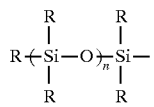

where all the depicted R groups are independently selected as alkyl or aryl groups having from 2 to about 10 carbon atoms that may be substituted or unsubstituted, straight-chained or branched, cyclic or acyclic, and may contain one or more catenary heteroatoms;

Z is an oxygen or sulfur atom or is of the formula —CO—, —COO—, —NH—, —CONH—, or —N(R)— where R is an substituted or unsubstituted alkyl or aryl group having from 1 to 10 carbon atoms that may contain catenary heteroatoms such as oxygen, sulfur, or nitrogen, and may contain one or more ethylene oxide groups; where R is an alkyl group, that alkyl group may be cyclic or acyclic; and x is a number selected such that the weight percent of ethylene oxide in the surfactant is between about 20 and 80 percent, preferably from about 40 to about 70 percent.

Representative hydrocarbon surfactants according to Formula II above include ethoxylated alkylphenols (such as the Triton™ TX, Igepal™ CA and Igepal™ CO series, commercially available from Union Carbide Corp. and Rhone-Poulenc Corp. respectively), ethoxylated dialkylphenols (such as the Igepal™ DM series, also commercially available from Rhone-Poulenc Corp.), ethoxylated fatty alcohols (such as the Tergitol™ series, commercially available from Union Carbide Corp.) and polyoxyethylene fatty acid diesters (such as the Mapeg™ DO series, commercially available from PPG Industries, Inc.).

Another class of non-fluorinated, nonionic polyoxyethylene-containing surfactants useful in combination with the fluoroaliphatic surfactants in accordance with the invention may be described by the following formula:

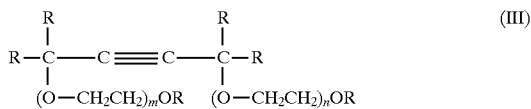

wherein:
- n and m are numbers between 2 and about 20 and are chosen such that the weight percent of polyoxyethylene in the surfactant is between 20 and 80 percent, preferably between 30 and 60 percent; and
- each R is selected independently from one another as an alkyl or an aryl group that may be substituted or unsubstituted and that contain from 2 to about 20 carbon atoms whose skeletal chain may be straight-chained, branched, or, if sufficiently large, cyclic, or any combination thereof; such skeletal chain can also optionally include one or more catenary heteroatoms such as oxygen, hexavalent sulfur, and trivalent nitrogen atoms bonded to the carbon atoms of the skeletal chain.

A third class of useful non-fluorinated, nonionic polyoxyethylene-containing surfactants useful in the practice of the invention in combination with the one or more fluoroaliphatic surfactants include those organosiloxane compounds that may be represented generally by the following formula:

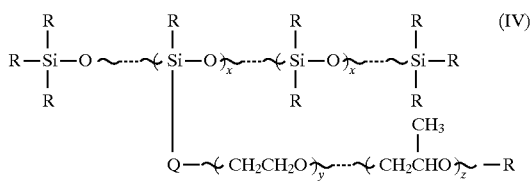

wherein:
- n, x, y, and z denote the number of repeating units in the depicted surfactant and are chosen such that the weight percent of polyethylene oxide in the surfactant is between 20 and 80 percent, preferably between 40 and 70 percent, and most preferably between 40 and 60 percent; It will be understood that the recurring siloxane units in the depicted formula may be randomly situated in the surfactant molecule;
- Q is a multivalent, generally divalent, linking group, or is a covalent bond, that provides a means to link the silicon atom to the depicted oxyalkylene group; Q can comprise a heteroatom-containing group, e.g., a group containing —O—, —CO—, —$C_nH_{2n}$O—, or —O$C_nH_{2n}$O—where n is a number from 1 to 6; and
- each R is selected independently from one another as an alkyl or an aryl group that may be substituted or unsubstituted and that contain from 2 to about 20 carbon atoms whose skeletal chain may be straight-chained, branched, or, if sufficiently large, cyclic, or any combination thereof, the skeletal chain can also optionally include one or more catenary heteroatoms such as oxygen, hexavalent sulfur, and trivalent nitrogen atoms bonded to the carbon atoms of the skeletal chain.

Useful silicone surfactants of the type depicted by Formula IV include ethoxylated polydimethylsiloxanes, such as Silwet™ L-77, commercially available from Union Carbide Corp.

The blends of fluorochemical surfactant and non-fluorochemical surfactant may be added to the thermoplastic resin in concentration ranges from about 0.2% to about 5.0% by weight. When nonwoven webs are prepared containing less than about 2.0 weight percent of surfactant blend, the blend is conveniently incorporated into the polymer by tumble blending the compound with resin pellets prior to extrusion or by metering liquid compound into the extruder hopper along with the resin pellets during extrusion. When greater than about 2.0 weight percent of surfactant blend is used, it is preferable to inject the compound into the molten polymer stream under high pressure either in the extruder barrel or immediately as the melt stream exits the extruder and before it enters the extrusion die. For convenience, a "master batch" or superconcentrate of surfactant blend in thermoplastic polymer can be made (e.g., thermoplastic resin containing 5–30 weight percent of surfactant blend which was melted and extruded into pellets) and added to the remaining thermoplastic polymer before the web extrusion process. Useful ratios of fluorochemical surfactant to non-fluorochemical surfactant are from 9:1 to 1:9, preferably from 8:2 to 2:8, more preferably from 8:2 to 4:6.

The fiber and fabrics of this invention can be used to prepare aqueous media absorbent articles such as diapers, feminine care products, and adult incontinence products, which utilize the fiber and fabrics as at least a portion of their fluid-absorbing "core" element. "Absorbent article" as used herein refers to a consumer product that is capable of absorbing significant quantities of water and other aqueous fluids (i.e., liquids) such as body fluids. Examples of aqueous media absorbent articles include disposable diapers, sanitary napkins, tampons, incontinence pads, disposable training pants, paper towels, geofabrics, facial tissues, medical drapes, medical gowns, and the like. The fabrics of the present invention are particularly suitable for use in articles like sanitary napkins, diapers, and incontinence pads.

Aqueous media absorbent articles frequently will comprise a substantially aqueous media impervious backing sheet, an aqueous media permeable top sheet and an aqueous absorbent core comprising an aqueous media absorbent structure position between said backing sheet and said top sheet. The impervious backing sheets may comprise any material, such as polyethylene or polypropylene, preferably having a thickness of at least about 0.038 mm, which will help retain fluid within the absorbent article. An impervious backing sheet may also comprise a fabric treated with a water repellent material. The permeable top sheets can comprise material, such as polyester, polyolefin, rayon, and the like, that is substantially porous and permits aqueous media to readily pass therethrough into the underlying absorbent core. Suitable materials for both the top sheets and the backing sheets are well known in the art.

More detailed descriptions of sanitary napkins and suitable materials for use therein may be found in U.S. Pat. Nos. 3,871,378 (Duncan et al.), 4,324,246 (Smith et al.), and 4,589,876 (Van Tillberg) all of whose descriptions are incorporated herein by reference.

Disposable diapers comprising the hydrophilic fabrics of the invention may be made by using conventional diaper making techniques, replacing or supplementing the wood pulp fiber core typically employed with the hydrophilic fabrics of the present invention. The hydrophilic polymers of the invention may also be used to input hydrophilicity to the top sheet of such an article where hydrophilicity is desired. The hydrophilic fabrics of this invention may thus be used in diapers in single layer or in multiple layer core configurations. Articles in the form of disposable diapers are described by U.S. Pat. Nos. 3,592,194 (Duncan et al.), 3,489,148 (Duncan et al.), and 3,860,003 (Buell), whose descriptions are also incorporated herein by reference.

The blends of fluorochemical surfactant and non-fluorochemical surfactant may be added to thermoplastic resin and the resin processed to create a durably hydrophilic film in accordance with conventional processing techniques. Such films may be non-porous or porous (including films that are mechanically perforated) selected according to desired performance characteristics. The resulting hydrophilic films find utility, for example, in the construction of femine hygiene products, battery separators among other uses.

The following examples are offered to aid in a better understanding of the present invention. These examples present and evaluate a number of useful surfactants according to the general formulas previously defined. This list is not to be construed as an exhaustive compilation of all surfactants useful in the present invention and the examples are not to be unnecessarily construed as limiting the scope of this invention.

EXAMPLES

Glossary

Fluoroaliphatic Group-containing Nonionic Compounds

F-1: $C_8F_{17}SO_2N(CH_3)C_2H_4OCH_2CH(OH)CH_2O(C_2H_4O)C_6H_4C(CH_3)_2CH_2C(CH_3)_2CH_3$. Compound F-1 was made according to the same general procedure as with Compound F-5, except that 140.86 g (0.22 eq) of MeFOSG was reacted with 58.74 g (0.22 eq) of Triton™ X-15 (an ethoxylated (1.0) alkylphenol, commercially available from Union Carbide Corp., Danbury, Conn.) in the presence of 0.624 g (0.54 mL, 0.0044 eq, or approximately 2.0 mole percent) of boron trifluoride etherate to provide the desired hydroxyether adduct, a liquid at room temperature.

F-2: $C_8F_{17}SO_2N(CH_3)C_2H_4OCH_2CH(OH)CH_2O(C_2H_4O)_{2.7}C_6H_4C(CH_3)_2CH_2C(CH_3)_2CH_3$. Compound F-2 was made according to the same general procedure as with Compound F-5, except that 64.03 g (0.1 eq) of MeFOSG was reacted with 33.8 g (0.1 eq) of Igepal™ CA-420 (an ethoxylated (2.7) alkylphenol, commercially available from Rhone-Poulenc Corp., Cranberry, N. J.) in the presence of 0.283 g (0.25 mL, 0.002 eq) of boron trifluoride etherate to provide the desired hydroxyether adduct, a liquid at room temperature.

F-3: $C_8F_{17}SO_2N(CH_3)C_2H_4OCH_2CH(OH)CH_2O(C_2H_4O)_5C_6H_4C(CH_3)_2CH_2C(CH_3)_2CH_3$. Compound F-3 was made according to the same general procedure as with Compound F-5, except that 64.03 g (0.1 eq) of MeFOSG was reacted with 42.6 g (0.1 eq) of Triton™ X-45 (an ethoxylated (5) alkylphenol, commercially available from Union Carbide Corp.) in the presence of 0.283 g (0.25 ML, 0.002 eq) of boron trifluoride etherate to provide the desired hydroxyether adduct, a liquid at room temperature.

F-4: $C_8F_{17}SO_2N(CH_3)C_2H_4OCH_2CH(OH)CH_2O(C_2H_4O)_{7.5}C_6H_4C(CH_3)_2CH_2C(CH_3)_2CH_3$. Compound F-4 was made according to the same general procedure as with Compound F-5, except that 96.63 g (0.15 eq) of MeFOSG was reacted with 81.9 g (0.15 eq) of Triton™ X-114 (an ethoxylated (7.5) alkylphenol, commercially available from Union Carbide Corp.) in the presence of 0.95 g (0.82 mL, 0.0066 eq) of boron trifluoride etherate to provide the desired hydroxyether adduct, a liquid at room temperature.

F-5: $C_8F_{17}SO_2N(CH_3)C_2H_4OCH_2CH(OH)CH_2O(C_2H_4O)_{9.5}C_6H_4C(CH_3)_2CH_2C(CH_3)_2CH_3$. Compound F-5 was made according to the following procedure. To a round-bottom flask equipped with a magnetic stir bar was added 96.63 g (0.15 eq) of molten

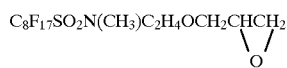

(MeFOSG, prepared by reacting $C_8F_{17}SO_2N(CH_3)H$ with epichlorohydrin using a procedure similar to that described in Example 1 of U.S. Pat. No. 5,380,778) and 95.1 g (0.15 eq) of Triton™ X-100 (an ethoxylated (9.5) alkylphenol, commercially available from Union Carbide Corp.), and the mixture was heated to 73° C. Next, while stirring, 0.4616 g (0.40 mL, approximately 2 mole percent) of boron trifluoride etherate (commercially available from Aldrich Chemical Co., Milwaukee, Wis.) was added in one portion to the mixture, which rose in temperature to a maximum of 88° C. after 8 minutes and then returned to 72° C. after 35 minutes. After approximately 2 hours, the reaction mixture was shown by gas chrmatographic analysis to contain no residual MeFOSG. Analysis of the reaction mixture by $^1H$ and $^{13}C$ NMR indicated that the mixture had reacted to completion to form the desired hydroxyether adduct, a liquid at room temperature.

F-6: $C_8F_{17}SO_2N(CH_3)C_2H_4OCH_2CH(OH)CH_2O(C_2H_4O)_{12.5}C_6H_4C(CH_3)_2CH_2C(CH_3)_2CH_3$. Compound F-6 was made according to the same general procedure as with Compound F-5, except that 96.6 g (0.15 eq) of MeFOSG was reacted with 114.9 g (0.15 eq) of Triton™ X-102 (an ethoxylated (12.5) alkylphenol, commercially available from Union Carbide Corp.) in the presence of 0.92 g (0.8 mL, 0.0065 eq) of boron trifluoride etherate to provide the desired hydroxyether adduct, a liquid at room temperature.

F-7: $C_8F_{17}SO_2N(CH_3)C_2H_4OCH_2CH(OH)CH_2O(C_2H_4O)_{30}C_6H_4C(CH_3)_2CH_2C(CH_3)_2CH_3$. Compound F-7 was made according to the same general procedure as with Compound F-5, except that 59.1 g (0.0923 eq) of MeFOSG was reacted with 140.85 g (0.0923 eq) of Triton™ X-305 (an ethoxylated (30) alkylphenol, commercially available from Union Carbide Corp.) in the presence of 0.38 g (0.33 mL, 0.0027 eq) of boron trifluoride etherate to provide the desired hydroxyether adduct, a liquid at room temperature.

F-8: $C_8F_{17}SO_2N(CH_3)C_2H_4OCH_2CH(OH)CH_2O(C_2H_4O)_8CH_3$. Compound F-8 was made according to the same general procedure as with Compound F-5, except that 64.4 g (0.1 eq) of MeFOSG was reacted with 35.0 g (0.1 eq) of Carbowax™ 350 (polyethylene glycol 350 monomethyl ether, commercially available from Union Carbide Corp.) in the presence of 0.115 g (0.1 mL, 0.0008 eq) of boron trifluoride etherate to provide the desired hydroxyether adduct, a liquid at room temperature.

F-9: $[C_8F_{17}SO_2N(CH_3)C_2H_4OCH_2CH(OH)CH_2]_3$—Thanol™ 4070. Compound F-9 was made according to the same general procedure as with Compound F-5, except that 33.21 g (0.05 eq) of MeFOSG was reacted with 77.1 g (0.05 eq) of Thanol™ 4070 (a 4626 molecular weight triol having in its backbone an 80/20 (wt) random copolymer of ethylene oxide and propylene oxide, commercially available from Union Carbide Corp.) in the presence of 0.173 g (0.15 mL, 0.00125 eq) of boron trifluoride etherate to provide the desired hydroxyether adduct, a liquid at room temperature.

F-10: $C_8F_{17}SO_2N(CH_3)C_2H_4OCH_2CH(OH)CH_2$—Igepal™ DM-530. Compound F-10 was made according to the same general procedure as with Compound F-5, except that 99.63 g (0.1546 eq) of MeFOSG was reacted with 111.3 g (0.15 eq) of Igepal™ DM-530 (commercially available from Rhone-Poulenc Corp., Cranberry, N.J.) in the presence of 0.53 g (0.46 mL, 0.00375 eq, 2.5 mole % with respect to MeFOSG) of boron trifluoride etherate to provide the desired hydroxyether adduct, a solid at room temperature.

F-11: $C_8F_{17}SO_2N(CH_3)C_2H_4OCH_2CH(OH)CH_2$—Igepal™ DM-710. Compound F-11 was made according to the same general procedure as with Compound F-5, except that 99.63 g (0.1546 eq) of MeFOSG was reacted with 149.1 g (0.15 eq) of Igepal™ DM-710 (commercially available from Rhone-Poulenc Corp.) in the presence of 1.38 g (1.20 mL, 0.0098 eq, 6.3 mole % with respect to MeFOSG) of boron trifluoride etherate to provide the desired hydroxyether adduct, a solid at room temperature.

F-12: $C_8F_{17}SO_2N(CH_3)C_2H_4OCH_2CH(OH)CH_2$—Igepal™ DM-880. Compound F-12 was made according to the same general procedure as with Compound F-5, except that 48.70 g (0.0.076 eq) of MeFOSG was reacted with 151.64 g (0.076 eq) of Igepal™ DM-880 (commercially available from Rhone-Poulenc Corp.) in the presence of 0.215 g (0.87 mL, 0.00153 eq, or 2 mole % with respect to MeFOSG) of boron trifluoride etherate to provide the desired hydroxyether adduct, a solid at room temperature.

F-13: $C_8F_{17}SO_2NHCH_2CH(OH)CH_2NHC(CH_3)CH_2[OC(CH_3)CH_2]_a\text{-}(OCH_2CH_2)_b[CH_2C(CH_3)NH]_cCH_2CH(OH)CH_2NHSO_2C_8F_{17}$, where a+c is approximately 2.5 and b is approximately 2.

Compound F-13 was made according to the same general procedure as used with Compound F-5, except that 64.42 g (0.1 eq) of MeFOSG was reacted with 32.86 g (0.1 eq) of Jeffamine™ ED-600 (commercially available from Huntsman Chemical Corp., Salt Lake City, Utah) in the presence of 0.14 g (0.122 mL, 0.001 eq) of boron trifluoride etherate to provide the desired adduct, a liquid at room temperature.

F-14: $C_8F_{17}SO_2NHCH_2CH(OH)CH_2NHC(CH_3)CH_2[OC(CH_3)CH_2]_a(OCH_2CH_2)_bCH_2C(CH_3)NHCH_2CH(OH)CH_2NHSO_2C_8F_{17}$, where a+c is approximately 2.5 and b is approximately 15.5.

Compound F-14 was made according to the same general procedure as used with Compound F-5, except that 64.42 g (0.1 eq) of MeFOSG was reacted with 50.5 g (0.1 eq) of Jeffamine™ ED-900 (commercially available from Huntsman Chemical Corp., Salt Lake City, Utah) in the presence of 0.14 g (0.122 mL, 0.001 eq) of boron trifluoride etherate to provide the desired adduct, a liquid at foom temperature.

F-15: Compound F-15, $C_8F_{17}SO_2N(C_2H_5)(C_2H_4O)_{7.3}H$, an ethoxylated fluoroaliphatic alcohol, was prepared according to U.S. Pat. No. 2,915,554 (Ahlbrecht et al.).

F-16: Compound F-16, Zonyl™ FSN, a tetrahydro fluorinated alkyl ethoxylate (CAS No. 65545-80-4), is commercially available from E. I. du Pont de Nemours & Co., Wilmington, Del.

F-17: Compound F-17, Zonyl™ FSO, a tetrahydro fluorinated alkyl ethoxylate, is commercially available from E.I. du Pont de Nemours & Co.

F-18: Compound F- 18, $C_8F_{17}SO_2N(CH_3)(C_2H_4O)_{9.5}C_6H_4C(CH_3)_2CH_2C(CH_3)_2CH_3$, was made according to the following procedure. To a 3 -necked roundbottom flask equipped with overhead stirrer, thermometer, reflux condensor and two attached gas washing bottles, the second bottle containing a 10% aqueous solution of sodium hydroxide, was charged 646 g (1.0 mole) of Triton™ X-100 and 12.9 g of Celite™ filter agent (commercially available from Aldrich Chemical Co.). The mixture was heated to 60° C., then 142.76 g (1.2 mole) of thionyl chloride was added via an addition funnel over a period of about 22 minutes, raising the mixture temperature to 75° C. Then nitrogen was bubbled through the reaction mixture for 4 hours, during which time the mixture temperature varied from 68°–71° C. The reflux condenser and gas washing bottles were replaced by a still head, and the reaction mixture was stirred while a vacuum of about 50 torr absolute pressure was applied. After the reaction was shown to be complete by $^{13}C$ and $^1H$ analysis of an aliquot, the reaction mixture was filtered hot through a C-porosity fritted glass Buchner funnel to yield a light yellow product, Triton™ X-100 chloride.

To a 3-necked round-bottom flask equipped with overhead stirrer, reflux condensor and nitrogen inlet adapter was charged 125 g (0.244 eq) of $C_8F_{17}SO_2NH_2$(MeFOSA), 177.80 g of Triton™ X-100 chloride (from the preparation given above), 30.18 g (0.2794 eq, a 15% molar excess) of sodium carbonate and 2.46 g (0.0149 eq, or 6.26 mole percent with respect to MeFOSA) of potassium iodide. The reaction mixture was heated to 120° C. for 8 hours, at which time the MeFOSA had disappeared according to analysis using gas chromatography. After cooling to 95° C., the reaction mixture was washed with 157 g of 10% aqueous sulfuric acid followed by 157 g of deionized water. The washed reaction mixture was concentrated by evaporation on a rotary evaporator at 70° C. and 50 torr absolute pressure to give 252.6 g of a brown liquid (92.2% yield), whose structure was characterized by 13C and 1H NMR spectroscopy to be consistent with the desired ether adduct.

F-19: $C_8F_{17}SO_2N(CH_3)$—Tergitol™ 15-S-9. Compound F-19 was made according to the same general procedure as with Compound F-18, except that 596 g (1.0eq) of Tergitol™ 15-S-9 ($C_{11\text{-}15}H_{23\text{-}31}(OCH_2CH_2)_9OH$, derived from a secondary alcohol, commercially available from Union Carbide Corp., Danbury, Conn.) was reacted with 142.76 g (1.2 eq) of thionyl chloride in the presence of 13 g of Celite™ filter agent to make the Tergitol™ 15-S-9 chloride.

Then 125 g (0.244 eq) of MeFOSA was reacted with 153.04 g (0.249 eq, or a 2% molar excess) of the Tergitol™ 15-S-9 chloride, 37.71 g (0.355 eq, or a 50% molar excess) of sodium carbonate and 3.57 g (0.022 eq, or 8.8 mole % with respect to MeFOSA) of potassium iodide to yield the desired ether adduct, a dark liquid.

F-20: $C_8F_{17}SO_2N(CH_3)$—Tergitol™ 15-S-12. Compound F-20 was made according to the same general procedure as with Compound F-18, except that 728 g (1.0 eq) of Tergitol™ 15-S-12 ($C_{11\text{-}15}H_{23\text{-}31}(OCH_2CH_2)_{12}OH$, derived from a secondary alcohol, commercially available from Union Carbide Corp., Danbury, Conn.) was reacted with 142.76 g (1.2 eq) of thionyl chloride in the presence of 14.56 g of Celite™ filter agent to make the Tergitol™ 15-S-12 chloride.

Then 125 g (0.244 eq) of MeFOSA was reacted with 185.91 g (0.249 eq, or a 2% molar excess) of the Tergitol™ 15-S-12 chloride, 37.71 g (0.355 eq, or a 50% molar excess) of sodium carbonate and 8.41 g (0.0205 eq, or 8.5 mole % with respect to MeFOSA) of potassium iodide to yield the desired ether adduct, a dark liquid.

F-21: $C_8F_{17}SO_2N(CH_3)$—Genapol™ 26-L-80.

Compound F-21 was made according to the same general procedure as with Compound F-18, except that 200.83 g (0.337 eq) of Genapol™ 26-L-80 ($C_{12\text{-}16}H_{25\text{-}33}(OCH_2CH_2)_{9.5}$ OH, derived from a primary alcohol, commercially available from Hoechst Celanese Corp., Charlotte, N.C.) was reacted with 48.12 g (0.4045 eq, a 20% molar excess) of thionyl chloride in the presence of 5.5 g of Celite™ filter agent to make the Genapol™ 26-L-80 chloride.

Then 125 g (0.244 eq) of MeFOSA was reacted with 179.93 g (0.249 eq, or a 2% molar excess) of the Genapol™ 26-L-80 chloride, 37.71 g (0.355 eq, or a 50% molar excess) of sodium carbonate and 2.76 g (0.0141 eq, or 8.5 mole % with respect to MeFOSA) of potassium iodide to yield the desired ether adduct, a straw-colored liquid.

F-22: $[C_8F_{17}SO_2N(CH_3)(C_2H_4O)_6C_2H_4]_2O$. Compound F-22 was made according to the same general procedure as with Compound F-18, except that 600 g (2.0 eq) of Carbowax™ 600 (polyethylene glycol, 600 molecular weight, commercially available from Union Carbide Corp., Danbury, Conn.) was reacted with 285.53 g (2.4 eq, a 20% molar excess) of thionyl chloride in the presence of 6 g of Celite™ filter agent to make the Carbowax™ 600 chloride.

Then 158.1 g (0.308 eq) of MeFOSA was reacted with 100.64 g (0.315 eq, or a 2% molar excess) of the Carbowax™ 600 chloride, 47.85 g (0.45 eq, or a 50% molar excess) of sodium carbonate and 5.46 g (0.0328 eq, or 10.6 mole % with respect to MeFOSA) of potassium iodide to yield the desired ether adduct, a solid at room temperature.

F-23: $C_8F_{17}SO_2N(CH_3)$—Igepal™ DM-530. Compound F-23 was made according to the same general procedure as with Compound F-18, except that 325.1 g (0.438 eq) of Igepal™ DM-530 (ethoxylated (9.6) branched dinonylphenol, available from Rhone-Poulenc Corp., Cranberry, N.J.) was reacted with 62.55 g (0.525 eq, a 20% molar excess) of thionyl chloride in the presence of 6.5 g of Celite™ filter agent to make the Igepal™ DM-530 chloride.

Then 138.59 g (0.270 eq) of MeFOSA was reacted with 200 g (0.263 eq, or a 3% molar deficiency) of the Igepal™ DM-530 chloride, 41.80 g (0.394 eq, or a 50% molar excess) of sodium carbonate and 2.73 g (0.0165 eq, or 6.1 mole % with respect to MeFOSA) of potassium iodide to yield the desired ether adduct, a solid at room temperature.

F-24: $C_8F_{17}SO_2N(CH_3)$—Igepal™ DM-710. Compound F-24 was made according to the same general procedure as with Compound F-18, except that 300.28 g (0.302 eq) of Igepal™ DM-710 (ethoxylated (15) branched dinonylphenol, available from Rhone-Poulenc Corp., Cranberry, N.J.) was reacted with 51.45 g (0.3635 eq, a 20% molar excess) of thionyl chloride in the presence of 6 g of Celite™ filter agent to make the Igepal™ DM-710 chloride.

Then 104.1 g (0.203 eq) of MeFOSA was reacted with 200 g (0.1975 eq, or a 3% molar deficiency) of the Igepal™ DM-710 chloride, 31.40 g (0.2962 eq, or a 50% molar excess) of sodium carbonate and 2.05 g (0.0123 eq, or 6.1 mole % with respect to MeFOSA) of potassium iodide to yield the desired ether adduct, a solid at room temperature.

F-25: $C_8F_{17}SO_2N(C_2H_5)C_2H_4OCH_2CH(OH)CH_2O(C_2H_4O)_{9.5}C_6H_4C(CH_3)_2CH_2C(CH_3)_2CH_3$. Compound F-25 was made according to the same general procedure as with Compound F-5, except that 62.84 g (0.1 eq) of

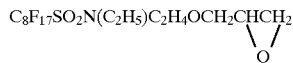

(EtFOSG, prepared by reacting $C_8F_{17}SO_2N(C_2H_5)H$ with epichlorohydrin using a procedure similar to that described in U.S. Pat. No. 5,025,052) was substituted for MeFOSG, 54.6 g (0.1 eq) of Triton™ X-100 was used, and 0.283 g (0.25 mL, 0.002 eq) of boron trifluoride etherate was used, yielding the desired hydroxyether adduct, a liquid at room temperature.

F-26: $C_8F_{17}SO_2N(C_2H_5)C_2H_4OCH_2CH(OH)CH_2O(C_2H_4O)_{7.5}C_6H_4C(CH_3)_2CH_2C(CH_3)_2CH_3$. Compound F-26 was made using a procedure similar to that used to make Compound F-4. Specifically, 62.84 g (0.1 eq) of EtFOSG was reacted with 54.6 g (0.1 eq) of Triton™ X-114 in the presence of 0.283 g (0.25 mL, 0.002 eq) of boron trifluoride etherate to yield the desired hydroxyether adduct, a liquid at room temperature.

F-27: $[C_8F_{17}SO_2N(C_2H_5)C_2H_4OCH_2CH(OH)CH_2]_3$—Thanol. Compound F-27 was made using a procedure similar to that used to make Compound F-9. Specifically, 31.42 g (0.05 eq) of EtFOSG was reacted with 77.1 g (0.05 eq) of Thanol™ 4070 in the presence of 0.173 g (0.15 mL, 0.00125 eq) of boron trifluoride etherate to yield the desired hydroxyether adduct, a liquid at room temperature.

F-28: $C_8F_{17}SO_2N(C_2H_5)C_2H_4OCH_2CH(OH)CH_2O(C_2H_4O)_8CH_3$. Compound F-28 was made using a procedure similar to that used to make Compound F-8. Specifically, 62.84 g (0.1 eq) of EtFOSG was reacted with 35.0 g (0.1 eq) of Carbowax™ 350 in the presence of 0.35 g (0.31 mL, 0.0025 eq) of boron trifluoride etherate to yield the desired hydroxyether adduct, a liquid at room temperature.

F-29: $C_8F_{17}SO_2N(C_2H_5)(C_2H_4O)_{9.5}C_6H_4C(CH_3)_2CH_2C(CH_3)_2CH_3$. Compound F-29 was made using a procedure similar to that used to make Compound F-18. Specifically, 4.004 kg (7.60 eq) of EtFOSA was reacted with 5.125 kg (7.712 eq, or a 1.015 equivalence ratio to the EtFOSA) of Triton™ X-100 chloride in the presence of 2.25 kg (2.79 eq) of sodium carbonate and 133 g (0.80 eq) of potassium iodide to yield the desired ether adduct, a liquid at room temperature.

F-30: $C_8F_{17}SO_2N(C_2H_5)$—Genapol™ 26-L-80. Compound F-30 was made using a procedure similar to that used to make Compound F-21. Specifically, 3.37 kg (6.4 eq) of EtFOSA was reacted with 4.0 kg (6.53 eq, or a 1.02 equivalence ratio to the EtFOSA) of Genapol™ 26-L-80 chloride in the presence of 0.814 kg (7.68 eq) of sodium carbonate and 79.7 g (0.48 eq) of potassium iodide to yield the desired ether adduct, a liquid at room temperature.

Hydrocarbon Group-containing, Nonionic Compounds
Ethoxylated Alkylphenols:

H-1: Triton™ X-15, ethoxylated (1) octylphenol, commercially available from Union Carbide Corp., Danbury, Conn. Triton™ X-15 contains approximately 17% by weight of polyethylene oxide.

H-2: Igepal™ CA-420, ethoxylated (2.7) octylphenol, commercially available from Rhone-Poulenc Corp., Cranberry, N.J. Igepal™ CA-420 contains approximately 37% by weight of polyethylene oxide.

H-3: Triton™ X-45, ethoxylated (5) octylphenol, commercially available from Union Carbide Corp. Triton™ X-45 contains approximately 52% by weight of polyethylene oxide.

H-4: Triton™ X-114, ethoxylated (7.5) octylphenol, commercially available from Union Carbide Corp. Triton™ X-114 contains approximately 62% by weight of polyethylene oxide.

H-5: Triton™ X-100, ethoxylated (9.5) octylphenol, commercially available from Union Carbide Corp. Triton™ X-100 contains approximately 67% by weight of polyethylene oxide.

H-6: Triton™ X-102, ethoxylated (12.5) octylphenol, commercially available from Union Carbide Corp. Triton™ X-102 contains approximately 73% by weight of polyethylene oxide.

H-7: Triton™ X-165, ethoxylated (16) octylphenol, commercially available from Union Carbide Corp. Triton™ X-165 contains approximately 77% by weight of polyethylene oxide.

H-8: Triton™ X-305, ethoxylated (30) octylphenol, commercially available from Union Carbide Corp. Triton™ X-305 contains approximately 87% by weight of polyethylene oxide.

H-9: Igepal™ RC-620, an ethoxylated (10) dodecylphenol, commercially available from Rhone-Poulenc Corp. Igepal™ RC-620 contains approximately 63% by weight of polyethylene oxide.

H-10: Igepal™ CO-710, ethoxylated (11) nonylphenol, commercially available from Rhone-Poulenc Corp. Igepal™ CO-710 contains approximately 79% by weight of polyethylene oxide.

Ethoxylated Dialkylphenols:

H-11: Igepal™ DM-530, ethoxylated (10) dinonylphenol, commercially available from Rhone-Poulenc Corp. Igepal™ DM-530 contains approximately 56% by weight of polyethylene oxide.

H-12: Igepal™ DM-710, ethoxylated (15) dinonylphenol, commercially available from Rhone-Poulenc Corp. Igepal™ DM-710 contains approximately 66% by weight of polyethylene oxide.

H-13: Igepal™ DM-880, ethoxylated (49) dinonylphenol, commercially available from Rhone-Poulenc Corp. Igepal™ DM-880 contains approximately 86% by weight of polyethylene oxide.

Ethoxylated Alcohols:

H-14: Tergitol™ 15-S-3, $C_{11-15}H_{23-31}(OCH_2CH_2)_3OH$, derived from a secondary alcohol, commercially available from Union Carbide Corp. Tergitol™ 15-S-3 contains approximately 40% by weight of polyethylene oxide.

H-15:Tergitol™ 15-S-9, $C_{11-15}H_{23-31}(OCH_2CH_2)_9OH$, derived from a secondary alcohol, commercially available from Union Carbide Corp. Tergitol™ 15-S-9 contains approximately 66% by weight of polyethylene oxide.

H-16: Genapol™ 26-L-80, $C_{12-16}H_{25-33}(OCH_2CH_2)_{9.5}OH$, derived from a primary alcohol, commercially available from Hoechst Celanese Corp., Charlotte, N.C. Genapol™ 26-L-80 contains approximately 66% by weight of polyethylene oxide.

H-17: Tergitol™ 15-S-12, $C_{11-15}H_{23-31}(OCH_2CH_2)_{12}OH$, derived from a secondary alcohol, commercially available from Union Carbide Corp. Tergitol™ 15-S-12 contains approximately 73% by weight of polyethylene oxide.

H-18: Tergitol™ 15-S-20, $C_{11-15}H_{23-31}(OCH_2CH_2)_{20}OH$, derived from a secondary alcohol, commercially available from Union Carbide Corp. Tergitol™ 15-S-20 contains approximately 81% by weight of polyethylene oxide.

H-19: Carbowax™ 350,polyethylene glycol 350 monomethyl ether, commercially available from Union Carbide Corp. Carbowax™ 350 contains approximately 92% by weight of polyethylene oxide.

Monoester Fatty Acid Ethoxylate:

H-20: Calgene™ 40-L, polyethylene glycol 400 monolaurate, commercially available from Calgene Chemical, Inc., Skokie, Ill. Calgene™ 40-L contains approximately 70% by weight of polyethylene oxide.

Diester Fatty Acid Ethoxylates:

H-21:Mapeg™ DO-400, polyethylene glycol 400 dioleate, commercially available from PPG Industries, Gurnee, Ill. Mapeg™ DO-400 contains approximately 42% by weight of polyethylene oxide.

H-22: Mapeg™ DO-600, polyethylene glycol 600 dioleate, commercially available from PPG Industries. Mapeg™ DO-600 contains approximately 52% by weight of polyethylene oxide.

Ethoxylated Amine:

H-23: Ethomeen™ C/15, an etboxylated (5) cocoamine forming a tertiary amine after thoxylation, commercially available from Akzo Chemicals Inc., Chicago, Ill. Ethomeen™ C/15 contains approximately 53% by weight of polyethylene oxide.

Ethoxylated Amides:

H-24: Witcamide™ M-3, a diethanol (2) cocoamide, commercially available from Witco Chemical corp., Chicago, Ill. Witcamide™ M-3 contains approximately 29% by weight of polyethylene oxide.

H-25: Ethomid™ O/17, an ethoxylated (5) oleoamide, commercially available from Akzo Chemicals Inc., Chicago, Ill. Ethomid™ O/17 contains approximately 42% by weight of polyethylene oxide.

EthoxUlated Mercaptans:

H-26: Alcodet™ 260, an ethoxylated (6) dodecylthiol, commercially available from Rhone-Poulenc Corp. Alcodet™ 260 contains approximately 47% by weight of polyethylene oxide.

H-27: Alcodet™ SK, an ethoxylated (8) dodecylthiol, commercially available from Rhone-Poulenc Corp. Alcodet™ SK contains approximately 54% by weight of polyethylene oxide.

H-28: Alcodet™ 218, an ethoxylated (10) dodecylthiol, commercially available from Rhone-Poulenc Corp. Alcodet™ 218 contains approximately 59% by weight of polyethylene oxide.

Acetylenic Diol Ethoxylates

H-29: Surfynol™ 420, an ethoxylated (1.3) acetylenic diol, commercially available from Air Products and Chemicals, Inc., Allentown, Pa. Surfynol™ 440 contains approximately 20% by weight of polyethylene oxide.

H-30: Surfynol™ 440, an ethoxylated (3.5) acetylenic diol, commercially available from Air Products and Chemicals, Inc., Allentown, Pa. Surfynol™ 440 contains approximately 40% by weight of polyethylene oxide.

H-31: Surfynol™ 465, an ethoxylated (10) acetylenic diol, commercially available from Air Products and Chemicals, Inc., Allentown, Pa. Surtynol™ 440 contains approximately 65% by weight of polyethylene oxide.

Sorbitol Esters:

H-32: Span™ 80, sorbitan monooleate, commercially available from ICI Americas Inc. Span™ 80 contains no polyethylene oxide.

H-33: Span™ 20, sorbitan monolaurate, commercially available from ICI Americas Inc. Span™ 20 contains no polyethylene oxide.

Ethoxylated Sorbitol Esters:

H-34: Tweenm™ 80, polyoxyethylene (20) sorbitan monooleate, commercially available from ICI Americas Inc. Tween™ 80 contains approximately 67% by weight of polyethylene oxide.

H-35: Tween™ 40, polyoxyethylene (20) sorbitan monolaurate, commercially available from ICI Americas Inc., Wilmington, Del. Tween™ 40 contains approximately 71% by weight of polyethylene oxide.

Propylene Oxide-Ethylene Oxide Block Copolymers

H-36: Pluronic™ L-63, polyoxypropylene/polyoxyethylene difunctional block copolymer, commercially available from BASF Corporation, Wyandotte, Minn. Pluronicm™ L-63 contains approximately 30% by weight of polyethylene oxide.

H-37: Tetronic™ 704, polyoxypropylene/polyoxyethylene tetrafunctional block copolymer, commercially available from BASF Corporation, Wyandotte, Minn. Tetronic™ 704 contains approximately 40% by weight of polyethylene oxide.

H-38: Pluronic™ L-3 5, polyoxypropylene/polyoxyethylene difunctional block copolymer, commercially available from BASF Corporation, Wyandotte, Minn. Pluronic™ L-35 contains approximately 50% by weight of polyethylene oxide.

Silicone-containing Ethoxylate Nonionic Compounds

S-1: NuWet™ 500, ethoxylated (14) silicone, commercially available from OSi Specialties, Inc., Danbury, Conn. NuWet™ 500 contains approximately 42% by weight of polyethylene oxide.

S-2: Tegropren™ 5840, polyoxyethylene-functional (13) silicone, has the general formula $(CH_3)_3SiO[Si(CH_3)_2O]_n$ $[Si(CH_3)(R)O]_mSi(CH_3)_3$, where n+m=1 and R, from analysis, was determined to be —$CH_2CH_2CH_2O$ $[CH_2CH_2O]_{13}[CH_2CH(CH_3)O]_6H$. Tegropren™ 5840 is conmmercially available from Goldschmidt Chemical Corporation, Hopewell, Va., and contains approximately 43% by weight of polyethylene oxide.

S-3: Silwet™ L-77, ethoxylated (7) silicone, commercially available from Union Carbide Corp. Silwet™ L-77 contains approximately 51% by weight of polyethylene oxide.

Thermoplastic Polymers

Escorene™ PP3505 Polypropylene—polypropylene, having a 400 melt flow rate, commercially available from Exxon Chemical Company, Houston, Tex.

Escorene™ PP3445 Polypropylene—polypropylene, having a 35 melt flow rate, commercially available from Exxon Chemical Company.

Aspun™ 6806 Polyethylene—polyethylene, having a melt index of 105 g/10 min (as measured by Test Method ASTM D-1238) and having a peak melting point of 124.8° C., commercially available from Dow Chemical Co., Midland, Mich.

Duraflex™ Polybutylene 8510—polybutylene polymer, having a 45 melt index (as measured by ASTM D1238, Condition D) and having a Brookfield viscosity of 640,000 cp (measured at 177° C. using a #29 spindle), commercially available from Shell Chemical Co., Houston, Tex.

Morthane™ PS 400—a thermoplastic polyurethane resin, having a Shore A Hardness (1 sec delay) of 89 and having a melting point range of 140°–210° C., commercially available from Shell Chemical Co.

Morthane™ Polyester-based Polyurethane PS440-200—a polyurethane resin, commercially available from Morton Thiokol Corp., Chicago, Ill.

Celanex™ 2002 Polybutylene Terephthalate—unfilled polybutylene terephthalate thermoplastic resin, medium flow, commercially available from Hoechst Celanese Corp., Chatham, N.J.

BASF Ultramid™ B3—nylon 6 polyamide resin, having a melting point of 220° C., having a number average molecular mass of 15000 and having a melt viscosity of 140 Pa·s at at 250° C. (D=1000 s$^{-1}$), commercially available from BASF Corp., Parsippany, N.J.

Test Methods

Melt-Blown Extrusion Procedure—The melt-blown extrusion procedure is the same as described in U.S. Pat. No. 5,300,357, column 10, which is herein incorporated by reference. The extruder used is a Brabender 42 mm conical twin screw extruder, with maximum extrusion temperature of 270°–280° C. and distance to the collector of 12 inches (30 cm).

Surfactant and thermoplastic polymer mixtures are mixed by tumble-blending the surfactant and thermoplastic polymer in a plastic bag for about five minutes until a visually homogeneous mixture is obtained.

The process condition for each mixture is the same, including the melt blowing die construction used to blow the microfiber web, the basis weight of the web (55±5 g/m$^2$) and the diameter of the microfibers (5–18 micrometers). Unless otherwise stated, the extrusion temperature is 200° C., the primary air temperature is 210° C., the pressure is 124 kPa (18 psi) (0.076 cm air gap width) and the polymer throughput rate is about 180 g/hr/cm.

Spun-Bond Extrusion Procedure—The extruder used is a Reifenhauser Extruder Model Number RT 381 (available from Reifenhauser Co., Troisdorf, Nordrhein Westfalen, Germany). The extruder is driven by an infinitely variable 3ø shunt wound DC motor, 37.3 kW & 2200 rev/min max. The maximum screw speed is reduced to 150 rev/min. The screw is 70 mm in diameter and 2100 mm in length. The entire extruder is 2.34 m in length by 1.335 m in width by 1.555 m in height, weighing 2200 kg. There are five 220 V heating zones at a total of 22.1 kW of heating power, giving a maximum heating zone temperature is 210° C.

The bonder is a Kusters Two-Bowl-Thermobonding-Calender (available from Kusters Corp., Nordrhein Westfalen, Germany). The effective bonding width is 1.2 m. The upper patterned metal roll has a 14.66% bonding area and a temperature of 270° F. (132° C.), while the lower rubber roll has a slick surface and a temperature of 265° F. (129° C.). The bonding nip pressure is 57–860 pounds force per linear inch (3000–46000 J/cm). The heating of the rolls of by convection from a continuously circulating furnace oil. The temperature range of the nips is 200°–300° F. (93°–149° C.). The bonder's speed is directly synchronized to the speed of the collection belt that has a range of 3.6 to 65 linear meters per minute.

The basis weight for the nonwoven web (g/m$^2$) can be calculated from the by multiplying the speed of the spin pump (rev/m) times the constant 71. For all examples, the basis weight used was approximately 20 g/m$^2$.

Hydrophilicity Test—The Hydrophilicity Test is run by holding a nonwoven web sample approximately 3×6 inches (7.6×15.2 cm) under a stream of either hot (approximately 45° C.) or cold (approximately 25° C.) tap water with a volume output of 200 mL/min at a distance of about 1 in (2.5 cm) from the water spigot. The following scale is used to rate hydrophilicity:

1—immediate wetting (most desirable situation)

2—wetting delayed for about 0.5–2.0 seconds

3—wetting delayed from greater than 2.0 seconds to about 10 seconds

4—wetting delayed from greater than 2.0 seconds to about 10 seconds, but only where the nonwoven sample contacts the hand placed under the sample 5—no wetting (least desirable situation)

Flux Test—The Flux Test is designed to measure the durability of the hydrophilically modified thermoplastic nonwoven web.

The test chamber consists of a glass cylinder 4 in (10 cm) in outside diameter and approximately 11 in (28 cm) tall, cut in half 5.6 in (14.2 cm) from the top and having attached at each newly cut edge a flange with outside diameter of 5.25 in (13.3 cm). The lips were created so that a 6 in by 6 in (15 cm by 15 cm) web sample could be clamped tightly in place between the flanges using four 3 in (7.6 cm) "bulldog" clamps and a gasket. A conical water deflector consisting of an inverted glass funnel of 3.55 in (9.0 cm) outside diameter is suspended in the cylinder at a height of approximately 6 inches (15 cm) over the web sample, and the cylinder is placed on a levelled polyethylene platform so that the web sample is perfectly horizontal. 200 mL of tap water at approximately 25° C. is poured over the conical deflector and a stop watch is started. The time for all of the water to penetrate the sample is measured. If incomplete penetration occurs within 5 minutes, the time is recorded as >300 seconds and the test is ended. If penetration occurs within 5 minutes, the time for penetration is recorded in seconds, the web sample is allowed to dry for 24 hours and the test is repeated the next day. Webs which wet very well will show penetration times of from 5–20 seconds. Webs showing durable wetting behavior will maintain those times after four consecutive days of flux testing.

Strikethrough Test—The Strikethrough Test is run to determine the time required for a given volume of surface-applied test liquid to enter and strikethrough a topsheet (made of hydrophilic nonwoven material) into an underlying absorbent core or absorbent pad. This test measures the efficiency of a topsheet in promptly allowing moisture to be absorbed by the core. This test is adapted from EDANA Test 150.2-93, "Liquid Strike-Through Time."

A core stack is constructed by stacking three sheets of Eaton Dikeman No. 939 filter paper, 4 inches (10.2 cm) in diameter. The stack is weighed and is placed matte side up on a plexiglass plate of 4 inches (10.2 cm)×4 inches (10.2 cm)×0.25 inches (0.64 cm) in dimensions. A 5 inch (12.7 cm) by 5 inch (12.7 cm) square cut from the hydrophilic nonwoven test material is placed, smooth side up, on top of the core stack. A strikethrough plate (described in EDANA Test 150.2-93), weighing 800 g and having red and black wires which connect to an electronic timer is placed on top of the test material.

To run the test, 5 mL of synthetic urine solution (prepared from Syn-Urine™ synthetic urine mixture as described by the vendor; the synthetic urine mixture commercially available from Endovations, Inc. Reading, Pa.), is dispensed from a burette and is allowed to drain into the strikethrough plate. This initial liquid flow completes the electrical circuit and starts the timer. The timer stops when the liquid has penetrated into the core stack and falls below the level of the electrodes. In this way, the time for the synthetic urine to drain through the test material is automatically recorded. A desirable strikethrough time is less than 4 seconds.

Rewet Test—The Rewet Test measures the quantity of liquid emerging through a previously wetted topsheet (made of hydrophilic nonwoven material) from a wet underlying hydrophilic core to cause removable wetness on the surface of the topsheet. This test provides an estimate how dry skin would remain when placed in contact with an absorbent structure containing the test topsheet. This test is adapted from EDANA Test 151.0-93, "Nonwoven Coverstock Wet-back."

Using the test set-up from the Strike Through Test, continue allowing more synthetic urine to drain into the strikethrough plate until the core stack is saturated. (The amount of test liquid required is calculated by multiplying the core stack weight by 3.9 load factor.) After the strikethrough cavity is allowed to drain completely, the strikethrough plate is removed and a weighed pickup stack, consisting of two stacked sheets of Eaton Dikeman No. 631 filter paper (5 inch (12.7 cm) by 5 inch) is placed on top of the remaining assembly and is topped by the wet hydrophilic nonwoven topsheet. A compression weight assembly, having square cross-sectional dimensions of 4 in (10.2 cm)×4 in (10.2 cm), is constructed by (a) stacking onto a 1 in (2.5 cm) thick, type A-30 polyurethane sponge a 0.25 in (0.63 cm) thick sheet of polymethyl methacrylate followed by an 8 pound (3.6 kg) weight, and (b) wrapping the stack with 1.2 mil polyethylene film. The resulting compression weight assembly is placed squarely on top of the pickup stack. The electronic timer is immediately started and, after 2 minutes, the assembly is taken apart to remove the pickup stack. The wet pickup stack is weighed and the amount of synthetic urine absorbed calculated by subtracting the weight of the dry pickup stack. A desirable rewet value is less than 0.5 g.

Percent Runoff Test—The Percent Runoff Test measures the amount of test liquid which is not absorbed when a predetermined amount of the liquid is poured onto the topsheet (made of hydrophilic nonwoven material) placed on an inclined table.

A "sandwich" is assembled as follows. Two pieces of Eaton-Dikeman #989 Filter Paper, Stock No. 1-04-0382) are placed directly one upon another, rough side up. A sample of hydrophilic topsheet is centered on top of the two-ply filter, with the sample extending approximately 0.25 in (0.64 cm) beyond the bottom edges of the filter papers. The edges of the "sandwich" are clipped to the top edge of a fixture which is an elevated flat plate having a 10° slope from horizontal, in such a way that the fabric overhang is "downhill". A separatory funnel containing 25 mL of Syn-Urine™ synthetic urine mixture is mounted on a ring stand so that the bottom of the funnel is centered over the "sandwich" at a 1 inch (2.5 cm) elevation and 0.5 in (1.3 cm) downhill from the clip. The stopcock of the separatory funnel is fully opened and the water is allowed to impinge upon the "sandwich", thus wetting both the nonwoven web and the filter papers. Water not absorbed by the "sandwich" is caught at the bottom of the incline in a catch basin. The amount of water in the catch basin is weighed, and the percent runoff is calculated by dividing the weight of water in catch basin by 25 and multiplying that quotient times 100.

Examples 1–31 and Comparative Examples C1–C23

In Examples 1–31 and Comparative Examples C1–C23, an experimental grid was run to measure the hydrophilicity of nonwoven polypropylene webs containing ethoxylated fluorochemical nonionic surfactants, ethoxylated octylphenols, and blends thereof, where the percent of ethylene oxide for each surfactant was varied. Surfactants and blends were each incorporated into Escorene™ PP3505 polypropylene at 1.00 weight percent, and nonwoven webs were extruded using the Melt-Blown Extrusion Procedure.

The hydrophilicity of each nonwoven web to hot and cold running tap water was determined using the Hydrophilicity Test, and the results of this study are presented in Table 1. The data were then examined for synergistic interaction between the fluorochemical and hydrocarbon surfactants.

Blends of fluorochemical and non-fluorochemical surfactants are considered "synergistic" in imparting hydrophilicity to a thermoplastic polymer when the hydrophilicity rating of the blend is at least as good as the best individual hydrophilicity rating for the fluorochemical or non-fluorochemical (in this case, hydrocarbon) surfactant, all measured at the same total surfactant concentration in the thermoplastic resin.

TABLE 1

| Example | Fluorochemical Surfactant | | Non-Fluorochemical Surfactant | | | Hydrophilicity | |
|---|---|---|---|---|---|---|---|
| | Name | # EO | Name | # EO | % PEO | Hot | Cold |
| C1 | — | — | H-1 | 1 | 18 | 5 | 5 |
| C2 | — | — | H-2 | 2.7 | 37 | 4 | 4 |
| C3 | — | — | H-3 | 5 | 52 | 4 | 5 |
| C4 | — | — | H-4 | 7.5 | 62 | 4 | 5 |
| C5 | — | — | H-5 | 9.5 | 67 | 4 | 5 |
| C6 | — | — | H-6 | 12.5 | 73 | 4 | 5 |

TABLE 1-continued

| Example | Fluorochemical Surfactant Name | # EO | Non-Fluorochemical Surfactant Name | # EO | % PEO | Hydrophilicity Hot | Cold |
|---|---|---|---|---|---|---|---|
| C7 | — | — | H-7 | 16 | 77 | 5 | 5 |
| C8 | — | — | H-8 | 30 | 87 | 5 | 5 |
| C9 | F-1 | 1 | — | — | — | 5 | 5 |
| C10 | F-1 | 1 | H-1 | 1 | 18 | 5 | 5 |
| 1 | F-1 | 1 | H-3 | 5 | 52 | 4 | 5 |
| 2 | F-1 | 1 | H-5 | 9.5 | 67 | 2 | 3 |
| C11 | F-1 | 1 | H-8 | 30 | 87 | 3 | 5 |
| C12 | F-2 | 2.7 | — | — | — | 4 | 5 |
| 3 | F-2 | 2.7 | H-2 | 2.7 | 37 | 3 | 5 |
| 4 | F-2 | 2.7 | H-3 | 5 | 52 | 2 | 5 |
| 5 | F-2 | 2.7 | H-4 | 7.5 | 62 | 1 | 2 |
| 6 | F-2 | 2.7 | H-5 | 9.5 | 67 | 1 | 3 |
| 7 | F-2 | 2.7 | H-6 | 12.5 | 73 | 1 | 3 |
| C13 | F-3 | 5 | — | — | — | 3 | 5 |
| C14 | F-3 | 5 | H-1 | 1 | 18 | 5 | 5 |
| 8 | F-3 | 5 | H-2 | 2.7 | 37 | 3 | 5 |
| 9 | F-3 | 5 | H-3 | 5 | 52 | 3 | 4 |
| 10 | F-3 | 5 | H-4 | 7.5 | 62 | 1 | 2 |
| 11 | F-3 | 5 | H-5 | 9.5 | 67 | 1 | 2 |
| 12 | F-3 | 5 | H-6 | 12.5 | 73 | 1 | 3 |
| 13 | F-3 | 5 | H-7 | 16 | 77 | 2 | 4 |
| C15 | F-3 | 5 | H-8 | 30 | 87 | 5 | 5 |
| C16 | F-4 | 7.5 | — | — | — | 2 | 4 |
| 14 | F-4 | 7.5 | H-2 | 2.7 | 37 | 2 | 3 |
| 15 | F-4 | 7.5 | H-3 | 5 | 52 | 1 | 3 |
| 16 | F-4 | 7.5 | H-4 | 7.5 | 62 | 1 | 2 |
| 17 | F-4 | 7.5 | H-5 | 9.5 | 67 | 1 | 3 |
| 18 | F-4 | 7.5 | H-6 | 12.5 | 73 | 1 | 2 |
| C17 | F-5 | 9.5 | — | — | — | 2 | 3 |
| C18 | F-5 | 9.5 | H-1 | 1 | 18 | 3 | 4 |
| 19 | F-5 | 9.5 | H-2 | 2.7 | 37 | 2 | 3 |
| 20 | F-5 | 9.5 | H-3 | 5 | 52 | 1 | 3 |
| 21 | F-5 | 9.5 | H-4 | 7.5 | 62 | 1 | 2 |
| 22 | F-5 | 9.5 | H-5 | 9.5 | 67 | 1 | 2 |
| 23 | F-5 | 9.5 | H-6 | 12.5 | 73 | 1 | 3 |
| 24 | F-5 | 9.5 | H-7 | 16 | 77 | 3 | 4 |
| C19 | F-5 | 9.5 | H-8 | 30 | 87 | 5 | 5 |
| C20 | F-6 | 12.5 | — | — | — | 1 | 3 |
| 25 | F-6 | 12.5 | H-2 | 2.7 | 37 | 2 | 4 |
| 26 | F-6 | 12.5 | H-3 | 5 | 52 | 1 | 3 |
| 27 | F-6 | 12.5 | H-4 | 7.5 | 62 | 1 | 3 |
| 28 | F-6 | 12.5 | H-5 | 9.5 | 67 | 1 | 3 |
| 29 | F-6 | 12.5 | H-6 | 12.5 | 73 | 2 | 3 |
| C21 | F-7 | 30 | — | — | — | 5 | 5 |
| C22 | F-7 | 30 | H-1 | 1 | 18 | 4 | 5 |
| 30 | F-7 | 30 | H-2 | 5 | 52 | 4 | 4 |
| 31 | F-7 | 30 | H-5 | 9.5 | 67 | 4 | 4 |
| C23 | F-7 | 30 | H-8 | 30 | 87 | 4 | 5 |

The data in Table 1 show that fluorocarbon surfactant F-5 at 1.00 wt % gave a measured hydrophilicity rating of 2 in hot water and 3 in cold water (Comparative Example C17), a rating designated as (2,3), while hydrocarbon surfactants (at 1 wt %) H-1, H-2, H-3, H-4, H-5, H-6, H-7 and H-8 with respectively 18, 37, 52, 62, 67, 73, 77 and 87 wt % polyethylene oxide gave hydrophilicity ratings of (5,5), (4,4), (4,5), (4,5), (4,5), (4,5), (4,5) and (5,5) respectively (Comparative Examples 1–8). The 50/50 blends of fluorochemical surfactant F-5 with each of H-2, H-3, H-4, H-5 and H-6 at a total level of 1.00 wt % (Examples 19, 20, 21, 22 and 23) gave, respectively, hydrophilicity ratings of (2,3), (1,3), (1,2), (1,2) and (1,3), all of which are at least as good as F-5 alone (Comparative Example C17), which has a hydrophilicity rating of (2,3).

The 50/50 blends of fluorochemical surfactant F-5 with hydrocarbon surfactants H-1, H-7 and H-8 (Comparative Examples C18, Example 24 and Comparative Example C19 respectively) gave hydrophilicity ratings of (3,4), (3,4) and (5,5) respectively; these blends are not considered synergistic in their hydrophilicity as their hydrophilicity ratings were worse than with F-5 alone (2,3) (Comparative Example C17).

Throughout Table 1, examples of synergy with the fluorochemical surfactants can be found with hydrocarbon surfactants H-2, H-3, H-4, H-5, H-6 and H-7, which contain from 33–77 wt % polyethylene oxide. Hydrocarbon surfactant H-1, containing only 18 wt % polyethylene oxide, shows synergy only with fluorochemical surfactant F-7 (Comparative Example C22) to give a hydrophilicity value of (4,5), compared to hydrophilicity values of (5,5) and (5,5) for H-I and F-7 alone (Comparative Examples C1 and C21 respectively), but this mild synergy is of low utility. Hydrocarbon surfactant H-8, containing 87 wt % polyethylene oxide, shows synergy with fluorochemical surfactants F-1 and F-7, giving hydrophilicity values of (3,5) and (4,5) (Comparative Examples C11 and C23 respectively), compared to hydrophilicity values of (5,5) for H-8, F-1 and F-7 measured alone (Comparative Examples C8, C9 and C21), but again, this mild synergy is of low utility.

Examples 32–55. and Comparative Examples C24–C65

In Examples 32–55, and Comparative Examples C24–C65, Fluorochemical Surfactant F-5 (the MeFOSG/Triton™ X-100 adduct), hydrocarbon and silicone surfactants, and blends thereof, were incorporated into Escorene™ PP3505 polypropylene at various wt % levels, and nonwoven webs were extruded using the Melt-Blown Extrusion Procedure.

The hydrophilicity of each nonwoven web was measured using the Hydrophilicity Test. Results from the Hydrophilicity Test are presented in Table 2.

TABLE 2

| Example | Fluorochemical Surfactant Name | wt % | Non-Fluorochemical Surfactant Name | # EO | % PEO | Hydrophilicity Hot | Cold |
|---|---|---|---|---|---|---|---|
| MeFOSG/Triton ™ X-100 adduct alone, (no hydrocarbon surfactant) | | | | | | | |
| C24 | F-5 | 1.00 | — | — | — | 2 | 3 |
| Akylphenol ethoxylates, alone and with MeFOSG/Triton ™ X-100 adduct | | | | | | | |
| C25 | — | — | H-5 | 1.00 | 67 | 4 | 5 |
| 32 | F-5 | 0.75 | H-5 | 0.25 | 67 | 1 | 1 |
| 33 | F-5 | 0.50 | H-5 | 0.50 | 67 | 1 | 1 |
| C26 | — | — | H-9 | 0.50 | 63 | 5 | 5 |
| 34 | F-5 | 0.50 | H-9 | 0.50 | 63 | 1 | 2 |
| C27 | — | — | H-10 | 1.00 | 79 | 4 | 4 |
| 35 | F-5 | 0.50 | H-10 | 0.50 | 79 | 1 | 2 |
| Dialkylphenols ethoxylates; alone and with MeFOSG/Triton ™ X-100 adduct | | | | | | | |
| C28 | — | — | H-11 | 1.00 | 56 | 5 | 5 |
| 36 | F-5 | 0.50 | H-11 | 0.50 | 56 | 1 | 2 |
| C29 | — | — | H-12 | 1.00 | 66 | 5 | 5 |
| 37 | F-5 | 0.50 | H-12 | 0.50 | 66 | 1 | 2 |
| C30 | — | — | H-13 | 1.00 | 86 | 5 | 5 |
| C31 | F-5 | 0.50 | H-13 | 0.50 | 86 | 5 | 5 |
| Ethoxylated alcohols, alone and with MeFOSG/Triton ™ X-100 adduct | | | | | | | |
| C32 | — | — | H-14 | 1.00 | 40 | 5 | 5 |
| 38 | F-5 | 0.50 | H-14 | 0.50 | 40 | 3 | 4 |
| C33 | — | — | H-15 | 1.00 | 69 | 5 | 5 |
| 39 | F-5 | 0.50 | H-15 | 0.50 | 69 | 1 | 2 |
| C34 | — | — | H-17 | 1.00 | 73 | 5 | 5 |
| 40 | F-5 | 0.50 | H-7 | 0.50 | 73 | 1 | 2 |

TABLE 2-continued

| Example | Fluorochemical Surfactant Name | wt % | Non-Fluorochemical Surfactant Name | # EO | % PEO | Hydrophilicity Hot | Cold |
|---|---|---|---|---|---|---|---|
| C35 | — | — | H-18 | 1.00 | 81 | 5 | 5 |
| C36 | F-5 | 0.50 | H-18 | 0.50 | 81 | 3 | 4 |
| Monoester fatty acid ethoxylates, alone and with MeFOSG/Triton ™ X-100 adduct | | | | | | | |
| C37 | — | — | H-20 | 1.00 | 70 | 4 | 4 |
| 41 | F-5 | 0.50 | H-20 | 0.50 | 70 | 3 | 4 |
| Diester fatty acid ethoxylates, alone and with MeFOSG/Triton ™ X-100 adduct | | | | | | | |
| C38 | — | — | H-21 | 1.00 | 42 | 5 | 5 |
| 42 | F-5 | 0.50 | H-21 | 0.50 | 42 | 3 | |
| C39 | — | — | H-22 | 1.00 | 52 | 5 | 5 |
| 43 | F-5 | 0.50 | H-22 | 0.50 | 52 | 1 | 1 |
| Ethoxylated amines, alone and with MeFOSG/Triton ™ X-100 adduct | | | | | | | |
| C40 | — | — | H-23 | 1.00 | 53 | 5 | 5 |
| 44 | F-5 | 0.50 | H-23 | 0.50 | 53 | 1 | 2 |
| Ethoxylated amides, alone and with MeFOSG/Triton ™ X-100 adduct | | | | | | | |
| C41 | — | — | H-24 | 1.00 | 29 | 5 | 5 |
| 45 | F-5 | 0.50 | H-24 | 0.50 | 29 | 1 | 3 |
| C42 | — | — | H-25 | 1.00 | 42 | 4 | 5 |
| 46 | F-5 | 0.50 | H-25 | 0.50 | 42 | 2 | 4 |
| Ethoxylated mercaptans, alone and with MeFOSG/Triton ™ X-100 adduct | | | | | | | |
| C43 | — | — | H-26 | 1.00 | 47 | 4 | 5 |
| 47 | F-5 | 0.50 | H-26 | 0.50 | 47 | 2 | 4 |
| C44 | — | — | H-27 | 1.00 | 54 | 5 | 5 |
| 48 | F-5 | 0.50 | H-27 | 0.50 | 54 | 1 | 2 |
| C45 | — | — | H-28 | 1.00 | 59 | 5 | 5 |
| 49 | F-5 | 0.50 | H-28 | 0.50 | 59 | 1 | 3 |
| Acetylenic diol ethoxylates, alone and with MeFOSG/Triton ™ X-100 adduct | | | | | | | |
| C46 | — | — | H-29 | 1.00 | 20 | 4 | 4 |
| 50 | F-5 | 0.50 | H-29 | 0.50 | 20 | 4 | 4 |
| C47 | — | — | H-30 | 1.00 | 40 | 5 | 5 |
| 51 | F-5 | 0.50 | H-30 | 0.50 | 40 | 2 | 3 |
| C48 | — | — | H-31 | 1.00 | 65 | 4 | 4 |
| 52 | F-5 | 0.50 | H-31 | 0.50 | 65 | 2 | 4 |
| Sorbitol esters, alone and with MeFOSG/Triton ™ X-100 adduct | | | | | | | |
| C49 | — | — | H-32 | 1.00 | 0 | 5 | 5 |
| C50 | F-5 | 0.50 | H-32 | 0.50 | 0 | 3 | 3 |
| C51 | — | — | H-33 | 1.00 | 0 | 4 | 4 |
| C52 | F-5 | 0.50 | H-33 | 0.50 | 0 | 2 | 3 |
| Ethoxylated sorbitol esters, alone and with MeFOSG/Triton ™ X-100 adduct | | | | | | | |
| C53 | — | — | H-34 | 2.50 | 67 | 3 | 4 |
| C54 | F-5 | 0.50 | H-34 | 0.50 | 67 | 5 | 5 |
| C55 | — | — | H-35 | 1.00 | 71 | 4 | 5 |
| C56 | F-5 | 0.50 | H-35 | 0.50 | 71 | 5 | 5 |
| PPO-PEO oxide block copolymers, alone and with MeFOSG/Triton ™ X-100 adduct | | | | | | | |
| C57 | — | — | H-36 | 1.00 | 30 | 5 | 5 |
| C58 | F-5 | 0.50 | H-36 | 0.50 | 30 | 5 | 5 |
| C59 | — | — | H-37 | 1.00 | 40 | 5 | 5 |
| C60 | F-5 | 0.50 | H-37 | 0.50 | 40 | 5 | 5 |
| C61 | — | — | H-38 | 1.00 | 50 | 3 | 4 |
| C62 | F-5 | 0.50 | H-38 | 0.50 | 50 | 5 | 5 |
| Silicone-containing ethoxylates, alone and with MeFOSG/Triton ™ X-100 adduct | | | | | | | |
| C63 | — | — | S-1 | 1.00 | 43 | 4 | 5 |
| 53 | F-5 | 0.50 | S-1 | 0.50 | 43 | 4 | 5 |
| C64 | — | — | S-2 | 1.00 | 43 | 1 | 3 |
| 54 | F-5 | 0.50 | S-2 | 0.50 | 43 | 1 | 1 |
| C65 | — | — | S-3 | 1.00 | 51 | 3 | 3 |
| 55 | F-5 | 0.50 | S-3 | 0.50 | 51 | 3 | 2 |

The data in Table 2 show that, in general, improved hydrophilicity was observed with fluorochemical surfactant/hydrocarbon surfactant combinations compared to the fluorochemical surfactant F-5 or the hydrocarbon surfactant run alone. Hydrocarbon surfactants H-14 (Tergitol™ 15-S-3), H-25 (Ethomid™ O/17) and H-26 (Alcodet™ 260) (Examples 38, 46 and 47 respectively) were the only hydrocarbon surfactants of this invention which did not exhibit hydrophilic synergism with fluorochemical surfactant F-5.

Hydrocarbon surfactants H-32 (Span™ 80), H-34 (Tween™ 80), H-36 (Pluronic™ L-63), H-37 (Tetronic™ 704) and H-38 (Pluronic™ L-35) did not perform synergistically (Comparative Examples C50, C54, C58, C60 and C62 respectively).

Hydrocarbon surfactants H-18 (Tergitol™ 15-S-20) and H-13 (Igepal™ DM-880) did not perform synergistically but are also outside the scope of this invention as they both contain over 80% by weight of polyethylene oxide.

Examples 56–61 and Comparative Examples C66–C72

In Examples 56–61 and Comparative Examples C66–C72, fluorochemical surfactants F-15 (alcohol ethoxylate), F-16 (Zonyl™ FSN), F-17 (Zonyl™ FSO); hydrocarbon surfactant H-5 (Triton™ X-100, ethoxylated octylphenol), and blends thereof, were incorporated into Escorene™ PP3505 polypropylene at 1.00 wt % and 0.75 wt % levels, and nonwoven webs were extruded using the Melt-Blown Extrusion Procedure.

The hydrophilicity of each nonwoven web was measured using the Hydrophilicity Test, with results presented in Table 3.

TABLE 3

| Example | Fluorochemical Surfactant Name | wt % | Non-Fluorochemical Surfactant Name | # EO | % PEO | Hydrophilicity Hot | Cold |
|---|---|---|---|---|---|---|---|
| Polypropylene (no surfactants used) | | | | | | | |
| C66 | — | — | — | — | — | 5 | 5 |
| Triton ™ X-100 alone (no fluorochemical surfactant) | | | | | | | |
| C67 | — | — | H-5 | 1.00 | 67 | 4 | 5 |
| Fluorochemical surfactants; alone and with Triton ™ X-100 | | | | | | | |
| C68 | F-15 | 1.00 | — | — | — | 1 | 1 |
| 56 | F-15 | 0.50 | H-5 | 0.50 | 67 | 1 | 1 |
| 57 | F-15 | 0.75 | H-5 | 0.25 | 67 | 1 | 1 |
| C69 | F-15 | 0.75 | — | — | — | 1 | 2 |
| 58 | F-15 | 0.50 | H-5 | 0.25 | 67 | 1 | 1 |
| C70 | F-16 | 1.00 | — | — | — | 1 | 1 |
| 59 | F-16 | 0.50 | H-5 | 0.50 | 67 | 1 | 1 |
| C71 | F-16 | 0.50 | — | — | — | 2 | 5 |
| 60 | F-16 | 0.40 | H-5 | 0.10 | 67 | 1 | 4 |
| C72 | F-17 | 1.00 | — | — | — | 1 | 1 |
| 61 | F-17 | 0.50 | H-5 | 0.50 | 67 | 1 | 1 |

The data in Table 3 show that in all cases a synergistic improvement in hydrophilicity was noted when fluorochemical surfactant F-15, F-16 or F-17 and hydrocarbon surfactant H-5 were added as a blend to the polypropylene.

Examples 62–68 and Comparative Examples C73–C85

In Examples 62–68 and Comparative Examples C73.C85, fluorochemical surfactant F-8 (MeFOSG/Carbowax™ 350 adduct), various hydrocarbon and silicone surfactants, and blends thereof, were incorporated into Escorene™ PP3505 polypropylene at various wt % levels, and nonwoven webs were extruded using the Melt-Blown Extrusion Procedure.

The hydrophilicity of each nonwoven web was measured using the Hydrophilicity Test, with results presented in Table 4.

TABLE 4

| | Fluorochemical Surfactant | | Non-Fluorochemical Surfactant | | | Hydrophilicity | |
|---|---|---|---|---|---|---|---|
| Example | Name | wt % | Name | # EO | % PEO | Hot | Cold |
| MeFOSG/Carbowax ™ 350 adduct, alone (no hydrocarbon surfactant) | | | | | | | |
| C73 | F-8 | 1.00 | — | — | — | 4 | 5 |
| Ethoxylated alkylphenol, alone and with MeFOSG/Carbowax ™ 350 adduct | | | | | | | |
| C74 | — | — | H-5 | 1.00 | 67 | 4 | 5 |
| 62 | F-8 | 0.75 | H-5 | 0.25 | 67 | 1 | 1 |
| 63 | F-8 | 0.50 | H-5 | 0.50 | 67 | 1 | 1 |
| Ethoxylated alcohol, alone and with MeFOSG/Carbowax ™ 350 adduct | | | | | | | |
| C75 | — | — | H-19 | 1.00 | 92 | 5 | 5 |
| C76 | F-8 | 0.50 | H-19 | 0.50 | 92 | 5 | 5 |
| Monoester fatty acid ethoxylate, alone and with MeFOSG/Carbowax ™ 350 adduct | | | | | | | |
| C77 | — | — | H-20 | 2.50 | 70 | 1 | 3 |
| 64 | F-8 | 0.50 | H-20 | 0.50 | 70 | 4 | 4 |
| Diester fatty acid ethoxylate, alone and with MeFOSG/Carbowax ™ 350 adduct | | | | | | | |
| C78 | — | — | H-21 | 1.00 | 42 | 5 | 5 |
| 65 | F-8 | 0.50 | H-21 | 0.50 | 42 | 1 | 1 |
| C79 | — | — | H-22 | 1.00 | 52 | 5 | 5 |
| 66 | F-8 | 0.50 | H-22 | 0.50 | 52 | 1 | 1 |
| Ethoxylated sorbitol ester, alone and with MeFOSG/Triton ™ X-100 adduct | | | | | | | |
| C80 | — | — | H-35 | 2.50 | 71 | 4 | 5 |
| C81 | F-8 | 0.50 | H-35 | 0.50 | 71 | 5 | 5 |
| Propylene oxide-ethylene oxide block copolymers, alone and with MeFOSG/Carbowax ™ 350 adduct | | | | | | | |
| C82 | — | — | H-38 | 2.50 | 50 | 3 | 4 |
| C83 | F-8 | 0.50 | H-38 | 0.50 | 50 | 5 | 5 |
| Silicone-containing ethoxylates, alone and with MeFOSG/Carbowax ™ 350 adduct | | | | | | | |
| C84 | — | — | S-2 | 1.00 | 43 | 1 | 3 |
| 67 | F-8 | 0.50 | S-2 | 0.50 | 43 | 1 | 1 |
| C85 | — | — | S-3 | 1.00 | 51 | 3 | 3 |
| 68 | F-8 | 0.50 | S-3 | 0.50 | 51 | 1 | 1 |

The data in Table 4 show that most all hydrocarbon and silicone surfactants in combination with fluorochemical surfactant F-10 showed synergistic activity in improving the hydrophilicity of polypropylene nonwoven webs.

Examples 69–70 and Comparative Examples C86–C88

In Examples 69–70 and Comparative Examples C86–C88, fluorochemical surfactants F-13 and F-14 (MeFOSG adducts to Jeffamine™ ED-600 and Jeffamine™ ED-900, respectively), ethoxylated alkylphenol surfactant H-5 (Triton™ X-100), and blends thereof, were incorporated into Escorene™ 3505 polypropylene at various wt % levels, and nonwoven webs were extruded using the Melt-Blown Extrusion Procedure.

The hydrophilicity of each nonwoven web was measured using the Hydrophilicity Test, with results presented in Table 5.

TABLE 5

| | Fluorochemical Surfactant | | Non-Fluorochemical Surfactant | | | Hydrophilicity | |
|---|---|---|---|---|---|---|---|
| Example | Name | wt % | Name | wt % | % PEO | Hot | Cold |
| Triton ™ X-100 alone (no fluorochemical surfactant) | | | | | | | |
| C68 | — | — | H-5 | 1.00 | 67 | 4 | 5 |
| Fluorochemical surfactants, alone and with Triton ™ X-100 | | | | | | | |
| C87 | F-13 | 1.00 | — | — | — | 4 | 5 |
| 69 | F-13 | 0.50 | H-5 | 0.50 | 67 | 1 | 3 |
| C88 | F-14 | 1.00 | — | — | — | 4 | 5 |
| 70 | F-14 | 0.50 | H-5 | 0.50 | 67 | 1 | 3 |

The data in Table 5 show that the blend of either fluorochemical surfactant F-13 or F-14 with hydrocarbon surfactant H-5 in polypropylene produced a synergistic improvement in hydrophilicity.

Examples 71–76 and Comparative Examples C89–C106

In Examples 71–76 and Comparative Examples C89–C106, fluorochemical surfactant F-9 (MeFOSG adduct to Thanol™ 4070), various hydrocarbon and silicone surfactants, and blends thereof, were incorporated into Escorene™ 3505 polypropylene at various wt % levels, and nonwoven webs were extruded using the Melt-Blown Extrusion Procedure.

The hydrophilicity of each nonwoven web was measured using the Hydrophilicity Test, with results presented in Table 6.

TABLE 6

| | Fluorochemical Surfactant | | Non-Fluorochemical Surfactant | | | Hydrophilicity | |
|---|---|---|---|---|---|---|---|
| Example | Name | wt % | Name | wt % | % PEO | Hot | Cold |
| Ethoxylated alkylphenol | | | | | | | |
| C89 | F-9 | 5.00 | — | — | — | 1 | 3 |
| C90 | — | — | H-5 | 5.00 | 67 | 4 | 5 |
| 71 | F-9 | 2.50 | H-5 | 2.50 | 67 | 1 | 2 |
| C91 | F-9 | 2.00 | — | — | — | 3 | 4 |
| C92 | — | — | H-5 | 2.00 | 67 | 4 | 5 |
| 72 | F-9 | 0.75 | H-5 | 0.75 | 67 | 1 | 4 |
| Monoester fatty acid ethoxylates | | | | | | | |
| C93 | F-9 | 2.00 | — | — | — | 3 | 4 |
| C94 | — | — | H-20 | 2.50 | 70 | 1 | 3 |
| 73 | F-9 | 1.50 | H-20 | 0.50 | 70 | 3 | 4 |
| Diester fatty acid ethoxylates | | | | | | | |
| C95 | F-9 | 2.00 | — | — | — | 3 | 4 |
| C96 | — | — | H-21 | 2.50 | 42 | 3 | 5 |

TABLE 6-continued

| | Fluorochemical Surfactant | | Non-Fluorochemical Surfactant | | | Hydrophilicity | |
|---|---|---|---|---|---|---|---|
| Example | Name | wt % | Name | wt % | % PEO | Hot | Cold |
| 74 | F-9 | 1.50 | H-21 | 0.50 | 42 | 5 | 5 |
| C97 | F-9 | 2.00 | — | — | — | 3 | 4 |
| C98 | — | — | H-22 | 2.50 | 52 | 5 | 5 |
| 75 | F-9 | 1.50 | H-22 | 0.50 | 52 | 1 | 4 |
| Ethoxylated sorbitol esters | | | | | | | |
| C99 | F-9 | 2.00 | — | — | — | 3 | 4 |
| C100 | — | — | H-35 | 2.50 | 50 | 4 | 5 |
| C101 | F-9 | 1.50 | H-35 | 0.50 | 50 | 4 | 5 |
| Propylene oxide-ethylene oxide block copolymer | | | | | | | |
| C102 | F-9 | 2.00 | — | — | — | 3 | 4 |
| C103 | — | — | H-38 | 2.50 | 50 | 3 | 4 |
| C104 | F-9 | 1.50 | H-38 | 0.50 | 50 | 4 | 5 |
| C105 | F-9 | 1.50 | — | — | — | 4 | 5 |
| C106 | — | — | S-2 | 1.00 | 43 | 1 | 3 |
| 76 | F-9 | 1.50 | S-2 | 0.50 | 43 | 3 | 4 |

The data in Table 6 show that the mixture of fluorochemical surfactant F-9 and hydrocarbon surfactant H-5 synergistically improved the hydrophilicity of the polypropylene over a total surfactant concentration range of 1.00 wt % to 5.00 wt %.

Hydrocarbon surfactant H-22 was also synergistic with fluorochemical surfactant F-9, but hydrocarbon surfactants H-21, H-20, H-35 and H-38 and silicone surfactant S-2 were not synergistic.

Examples 77–86 and Comparative Examples C107–C126

In Examples 77–86 and Comparative Examples C107–C126, fluorochemical surfactant F-18 (MeFOSA adduct to Triton™ X-100), various hydrocarbon surfactants, and blends thereof, were incorporated into Escorene™ 3505 polypropylene at various wt % levels, and nonwoven webs were extruded using the Melt-Blown Extrusion Procedure.

The hydrophilicity of each nonwoven web was measured using the Hydrophilicity Test, with results presented in Table 7.

TABLE 7

| | Fluorochemical Surfactant | | Non-Fluorochemical Surfactant | | | Hydrophilicity | |
|---|---|---|---|---|---|---|---|
| Example | Name | wt % | Name | wt % | % PEO | Hot | Cold |
| Ethoxylated alkylphenols | | | | | | | |
| C107 | F-18 | 5.00 | — | — | — | 1 | 1 |
| C108 | — | — | H-5 | 4.00 | 67 | 4 | 5 |
| 77 | F-18 | 2.50 | H-5 | 2.50 | 67 | 1 | 1 |
| C109 | F-18 | 1.00 | — | — | — | 1 | 2 |
| C110 | — | — | H-5 | 1.00 | 67 | 4 | 5 |
| 78 | F-18 | 0.50 | H-5 | 0.50 | 67 | 1 | 1 |
| Ethoxylated dialkylphenols | | | | | | | |
| C111 | F-18 | 1.00 | — | — | — | 1 | 2 |
| C112 | — | — | H-11 | 1.00 | 56 | 5 | 5 |
| 79 | F-18 | 0.50 | H-11 | 0.50 | 56 | 2 | 3 |
| C113 | F-18 | 1.00 | — | — | — | 1 | 2 |
| C114 | — | — | H-12 | 1.00 | 66 | 5 | 5 |
| 80 | F-18 | 0.50 | H-12 | 0.50 | 66 | 2 | 4 |

TABLE 7-continued

| | Fluorochemical Surfactant | | Non-Fluorochemical Surfactant | | | Hydrophilicity | |
|---|---|---|---|---|---|---|---|
| Example | Name | wt % | Name | wt % | % PEO | Hot | Cold |
| Ethoxylated alcohols | | | | | | | |
| C115 | F-18 | 1.00 | — | — | — | 1 | 2 |
| C116 | — | — | H-15 | 1.00 | 66 | 4 | 5 |
| 81 | F-18 | 0.50 | H-15 | 0.50 | 66 | 1 | 1 |
| C117 | F-18 | 1.00 | — | — | — | 1 | 2 |
| C118 | — | — | H-16 | 1.00 | 66t | 4 | 5 |
| 82 | F-18 | 0.50 | H-16 | 0.50 | 66 | 1 | 1 |
| C119 | F-18 | 1.00 | — | — | — | 1 | 2 |
| C120 | — | — | H-17 | 1.00 | 73 | 5 | 5 |
| 83 | F-18 | 0.50 | H-17 | 0.50 | 73 | 2 | 5 |
| Monoester fatty ester ethoxylates | | | | | | | |
| C121 | F-18 | 1.00 | — | — | — | 1 | 2 |
| C122 | — | — | H-20 | 1.00 | 70 | 4 | 4 |
| 84 | F-18 | 0.50 | H-20 | 0.50 | 70 | 2 | 2 |
| Diester fatty ester ethoxylates | | | | | | | |
| C123 | F-18 | 1.00 | — | — | — | 1 | 2 |
| C123 | — | — | H-21 | 1.00 | 42 | 5 | 5 |
| 85 | F-18 | 0.50 | H-21 | 0.50 | 42 | 1 | 1 |
| C125 | F-18 | 1.00 | — | — | — | 1 | 2 |
| C126 | — | — | H-22 | 1.00 | 52 | 5 | 5 |
| 86 | F-18 | 0.50 | H-22 | 0.50 | 52 | 1 | 1 |

The data in Table 7 show that, with the exception of hydrocarbon surfactant H-17 (Tergitol™ 15-S-12), H-11 (Igepal™ DM-530), H-12 (Igepal™ DM-710) and possibly H-20 (Calgene™ 40-L), the mixture of fluorochemical surfactant F-18 and each hydrocarbon surfactant synergistically improved the hydrophilicity of the polypropylene over a total surfactant concentration range of 1.00 wt % to 5.00 wt %.

Examples 87–96 and Comparative Examples C127–142

In Examples 87–96 and Comparative Examples C127–C142, fluorochemical surfactants F-19 (MeFOSA adduct to Tergitol™ 15-S-9) and F-20 (MeFOSA adduct to Tergitol™ 15-S-12); hydrocarbon surfactants H-5 (Triton™ X-100, ethoxylated octylphenol) and H-21 and H-22 (Mapeg™ DO-400 and Mapeg™ DO600, polyethylene glycol dioleates); and blends thereof were incorporated into Escorene™ 3505 polypropylene at various wt % levels, and nonwoven webs were extruded using the Melt-Blown Extrusion Procedure.

The hydrophilicity of each nonwoven web was measured using the Hydrophilicity Test, with results presented in Table 8.

TABLE 8

| | Fluorochemical Surfactant | | Non-Fluorochemical Surfactant | | | Hydrophilicity | |
|---|---|---|---|---|---|---|---|
| Example | Name | wt % | Name | wt % | % PEO | Hot | Cold |
| Ethoxylated alkylphenols | | | | | | | |
| C127 | F-19 | 1.00 | — | — | — | 1 | 2 |
| C128 | — | — | H-5 | 1.00 | 67 | 4 | 5 |
| 87 | F-19 | 0.50 | H-5 | 0.50 | 67 | 1 | 1 |
| C129 | F-19 | 0.75 | — | — | — | 2 | 4 |

TABLE 8-continued

| Example | Fluorochemical Surfactant Name | wt % | Non-Fluorochemical Surfactant Name | wt % | % PEO | Hydrophilicity Hot | Cold |
|---|---|---|---|---|---|---|---|
| C130 | — | — | H-5 | 1.00 | 67 | 4 | 5 |
| 88 | F-19 | 0.25 | H-5 | 0.50 | 67 | 2 | 5 |
| 89 | F-19 | 0.38 | H-5 | 0.38 | 67 | 2 | 5 |
| 90 | F-19 | 0.50 | H-5 | 0.25 | 67 | 2 | 4 |
| C131 | F-20 | 1.00 | — | — | — | 1 | 1 |
| C132 | — | — | H-5 | 1.00 | 67 | 4 | 5 |
| 95 | F-20 | 0.50 | H-5 | 0.50 | 67 | 1 | 1 |
| C133 | F-20 | 0.75 | — | — | — | 1 | 2 |
| C134 | — | — | H-5 | 1.00 | 67 | 4 | 5 |
| 92 | F-20 | 0.50 | H-5 | 0.25 | 67 | 1 | 2 |
| C135 | F-20 | 0.63 | — | — | — | 2 | 2 |
| C136 | — | — | H-5 | 1.00 | 67 | 4 | 5 |
| 93 | F-20 | 0.47 | H-5 | 0.16 | 67 | 2 | 4 |
| Diester fatty acid ethoxylates | | | | | | | |
| C137 | F-20 | 1.00 | — | — | — | 1 | 1 |
| C138 | — | — | H-21 | 1.00 | 42 | 5 | 5 |
| 94 | F-20 | 0.50 | H-21 | 0.50 | 42 | 1 | 1 |
| C139 | F-19 | 1.00 | — | — | — | 1 | 2 |
| C140 | — | — | H-22 | 1.00 | 52 | 5 | 5 |
| 95 | F-19 | 0.50 | H-22 | 0.50 | 52 | 1 | 1 |
| C141 | F-20 | 1.00 | — | — | — | 1 | 1 |
| C142 | — | — | H-22 | 1.00 | 52 | 5 | 5 |
| 96 | F-20 | 0.50 | H-22 | 0.50 | 52 | 1 | 1 |

The data in Table 8 show that, at 1.00 wt % in polypropylene, most surfactant blends showed synergistic improvement in hydrophilicity compared to each hydrocarbon and fluorochemical surfactant used alone.

Examples 97–100 and Comparative Examples C143–C150

In Examples 97–100 and Comparative Examples C143–C150, fluorochemical surfactants F-21 (MeFOSA adduct to Genapol™ 26-L-80) and F-22 (MeFOSA adduct to Carbowax™ 600); hydrocarbon surfactants H-5 (Triton™ X-100, ethoxylated octylphenol) and H-21 and H-22 (Mapeg™ DO-400 and Mapeg™ DO-600, polyethylene glycol dioleates); and blends thereof were incorporated into Escorene™ 3505 polypropylene at various wt % levels, and nonwoven webs were extruded using the Melt-Blown Extrusion Procedure.

The hydrophilicity of each nonwoven web was measured using the Hydrophilicity Test, with results presented in Table 9.

TABLE 9

| Example | Fluorochemical Surfactant Name | wt % | Non-Fluorochemical Surfactant Name | wt % | % PEO | Hydrophilicity Hot | Cold |
|---|---|---|---|---|---|---|---|
| Ethoxylated alkylphenols | | | | | | | |
| C143 | F-21 | 1.00 | — | — | — | 1 | 1 |
| C144 | — | — | H-5 | 1.00 | 67 | 4 | 5 |
| 97 | F-21 | 0.50 | H-5 | 0.50 | 67 | 1 | 3 |
| C145 | F-22 | 1.00 | — | — | — | 2 | 4 |
| C146 | — | — | H-5 | 1.00 | 67 | 4 | 5 |
| 98 | F-22 | 0.50 | H-5 | 0.50 | 67 | 1 | 1 |
| Diester fatty acid ethoxylates | | | | | | | |
| C147 | F-21 | 1.00 | — | — | — | 1 | 1 |
| C148 | — | — | H-21 | 1.00 | 42 | 5 | 5 |
| 99 | F-21 | 0.50 | H-21 | 0.50 | 42 | 3 | 5 |
| C149 | F-21 | 1.00 | — | — | — | 1 | 1 |
| C150 | — | — | H-22 | 1.00 | 52 | 5 | 5 |
| 100 | F-21 | 0.50 | H-22 | 0.50 | 52 | 1 | 3 |

The data in Table 9 show that, when mixed with hydrocarbon surfactant, fluorochemical surfactant F-22 exhibited synergism but fluorochemical surfactant F-21 did not.

Examples 101–113 and Comparative Examples C151–C176

In Examples 101–113 and Comparative Examples C151–C176, fluorochemical surfactants F-23 (MeFOSA adduct to Igepal™ DM-530), F-24 (MeFOSA adduct to Igepal™ DM-710, F-10 (MeFOSG adduct to Igepal™ DM-530), F-11 (MeFOSG adduct to Igepal™ DM-710), and F-12 (MeFOSG adduct to Igepal™ DM-880); hydrocarbon surfactants H-5 (Triton™ X-100, ethoxylated octylphenol) and H-11 and H-12 (Igepal™ DM-530 and Igepal™ DM-710, ethoxylated dialkylphenols); and blends thereof were incorporated into Escorene™ 3505 polypropylene at various wt % levels, and nonwoven webs were extruded using the Melt-Blown Extrusion Procedure.

The hydrophilicity of each nonwoven web was measured using the Hydrophilicity Test, with results presented in Table 10.

TABLE 10

| Example | Fluorochemical Surfactant Name | wt % | Non-Fluorochemical Surfactant Name | wt % | % PEO | Hydrophilicity Hot | Cold |
|---|---|---|---|---|---|---|---|
| Ethoxylated alkylphenols | | | | | | | |
| C151 | F-23 | 5.00 | — | — | — | 1 | 3 |
| C152 | — | — | H-5 | 4.00 | 67 | 4 | 5 |
| 101 | F-23 | 2.50 | H-5 | 2.50 | 67 | 1 | 1 |
| C153 | F-23 | 1.00 | — | — | — | 5 | 5 |
| C154 | — | — | H-5 | 1.00 | 67 | 4 | 5 |
| 102 | F-23 | 0.50 | H-5 | 0.50 | 67 | 4 | 5 |
| C155 | F-24 | 5.00 | — | — | — | 1 | 1 |
| C156 | — | — | H-5 | 4.00 | 67 | 4 | 5 |
| 103 | F-24 | 2.00 | H-5 | 2.50 | 67 | 1 | 1 |
| C157 | F-24 | 1.00 | — | — | — | 3 | 5 |
| C158 | — | — | H-5 | 1.00 | 67 | 4 | 5 |
| 104 | F-24 | 0.50 | H-5 | 0.50 | 67 | 4 | 5 |
| C159 | F-10 | 1.00 | — | — | — | 5 | 5 |
| C160 | — | — | H-5 | 1.00 | 67 | 4 | 5 |
| 105 | F-10 | 0.50 | H-5 | 0.50 | 67 | 3 | 5 |
| C161 | F-11 | 1.00 | — | — | — | 5 | 5 |
| C162 | — | — | H-5 | 1.00 | 67 | 4 | 5 |
| 106 | F-11 | 0.50 | H-5 | 0.50 | 67 | 5 | 5 |
| C163 | F-12 | 1.00 | — | — | — | 5 | 5 |
| C164 | — | — | H-5 | 1.00 | 67 | 4 | 5 |
| 107 | F-12 | 0.50 | H-5 | 0.50 | 67 | 5 | 5 |
| Ethoxylated dialkylphenols | | | | | | | |
| C165 | F-23 | 1.00 | — | — | — | 5 | 5 |
| C166 | — | — | H-11 | 1.00 | 56 | 5 | 5 |
| 108 | F-23 | 0.50 | H-11 | 0.50 | 56 | 5 | 5 |
| C167 | F-24 | 1.00 | — | — | — | 3 | 5 |
| C168 | — | — | H-11 | 1.00 | 56 | 5 | 5 |
| 109 | F-24 | 0.50 | H-11 | 0.50 | 56 | 4 | 5 |

TABLE 10-continued

| Example | Fluorochemical Surfactant Name | wt % | Non-Fluorochemical Surfactant Name | wt % | % PEO | Hydrophilicity Hot | Cold |
|---|---|---|---|---|---|---|---|
| C169 | F-10 | 1.00 | — | — | — | 5 | 5 |
| C170 | — | — | H-11 | 1.00 | 56 | 5 | 5 |
| 110 | F-10 | 0.50 | H-11 | 0.50 | 56 | 4 | 5 |
| C171 | F-23 | 1.00 | — | — | — | 5 | 5 |
| C172 | — | — | H-12 | 1.00 | 66 | 5 | 5 |
| 111 | F-23 | 0.50 | H-12 | 0.50 | 66 | 5 | 5 |
| C173 | F-24 | 1.00 | — | — | — | 3 | 5 |
| C174 | — | — | H-12 | 1.00 | 66 | 5 | 5 |
| 112 | F-24 | 0.50 | H-12 | 0.50 | 66 | 4 | 5 |
| C175 | F-11 | 1.00 | — | — | — | 5 | 5 |
| C176 | — | — | H-12 | 1.00 | 66 | 5 | 5 |
| 113 | F-11 | 0.50 | H-12 | 0.50 | 66 | 5 | 5 |

The data in Table 10 show that, at both 1.00 and 5.00 wt % in polypropylene, blends of all the fluorochemical surfactants with hydrocarbon surfactant H-5 show synergistic improvement in hydrophilicity except for fluorochemical surfactants F-11 and F-12, which contain a high percentage of ethylene oxide. However, with fluorochemical surfactants F-23 and F-24, the higher concentration of 5 wt % (Examples 101 and 103 respectively) gave better synergy than did the lower concentration of 1 wt % (Examples 102 and 104).

Examples 114–121 and Comparative Examples C179–C 192

In Examples 114–121 and Comparative Examples C179–C192, N-ethyl substituted sulfonamide fluorochemical surfactants F-25 to F-28 (ethylene oxide adducts to EtFOSG,

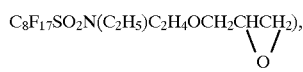

and F-29 and F-30 (ethylene oxide adducts to EtFOSA, $C_8F_{17}SO_2N(C_2H_5)H$); hydrocarbon surfactants H-4 and H-5 (Triton™ X-114 and Tritonr™ X-100, ethoxylated octylphenols) hydrocarbon surfactants H-11 and H-12 (Igepal™ DM-530 and Igepal™ DM-710, ethoxylated dialkylphenols); and blends thereof were incorporated into Escorene™ 3505 polypropylene at various wt % levels, and nonwoven webs were extruded using the Melt-Blown Extrusion Procedure.

The hydrophilicity of each nonwoven web was measured using the Hydrophilicity Test, with results presented in Table 11.

TABLE 11

| Example | Fluorochemical Surfactant Name | wt % | Non-Fluorochemical Surfactant Name | wt % | % PEO | Hydrophilicity Hot | Cold |
|---|---|---|---|---|---|---|---|
| Ethoxylated alkylphenols | | | | | | | |
| C177 | F-26 | 1.00 | — | — | — | 2 | 3 |
| C178 | — | — | H-4 | 1.00 | 62 | 4 | 5 |
| 114 | F-26 | 0.50 | H-4 | 0.50 | 62 | 1 | 1 |
| C179 | F-25 | 1.00 | — | — | — | 1 | 2 |
| C180 | — | — | H-5 | 1.00 | 67 | 4 | 5 |
| 115 | F-25 | 0.50 | H-5 | 0.50 | 67 | 1 | 2 |

TABLE 11-continued

| Example | Fluorochemical Surfactant Name | wt % | Non-Fluorochemical Surfactant Name | wt % | % PEO | Hydrophilicity Hot | Cold |
|---|---|---|---|---|---|---|---|
| C181 | F-27 | 1.00 | — | — | — | 3 | 5 |
| C182 | — | — | H-5 | 1.00 | 67 | 4 | 5 |
| 116 | F-27 | 0.50 | H-5 | 0.50 | 67 | 3 | 5 |
| C183 | F-28 | 1.00 | — | — | — | 4 | 5 |
| C184 | — | — | H-5 | 1.00 | 67 | 4 | 5 |
| 117 | F-28 | 0.50 | H-5 | 0.50 | 67 | 1 | 1 |
| C185 | F-29 | 1.00 | — | — | — | 2 | 2 |
| C186 | — | — | H-5 | 1.00 | 67 | 4 | 5 |
| 118 | F-29 | 0.50 | H-5 | 0.50 | 67 | 1 | 2 |
| C187 | F-30 | 1.00 | — | — | — | 1 | 2 |
| C188 | — | — | H-5 | 1.00 | 67 | 4 | 5 |
| 119 | F-30 | 0.50 | H-5 | 0.50 | 67 | 2 | 3 |
| Ethoxylated dialkylphenols | | | | | | | |
| C189 | F-25 | 1.00 | — | — | — | 1 | 2 |
| C190 | — | — | H-11 | 1.00 | 56 | 5 | 5 |
| 120 | F-25 | 0.50 | H-11 | 0.50 | 56 | 1 | 2 |
| C191 | F-25 | 1.00 | — | — | — | 1 | 2 |
| C192 | — | — | H-12 | 1.00 | 66 | 5 | 5 |
| 121 | F-25 | 0.50 | H-12 | 0.50 | 66 | 1 | 1 |

The data in Table 11 show that, with the exception of F-30, blends of all the N-ethyl sulfonamido fluorochemical surfactants with hydrocarbon surfactants show synergistic improvement in hydrophilicity.

Examples 122–129 and Comparative Examples C193–C204

In Examples 122–129 and Comparative Examples C193–C204, fluorochemical surfactants F-5 (MeFOSG/Triton™ X-100 adduct), F-8 (MeFOSG/Carbowax™ 350 adduct) and F-9 (MeFOSG adduct to Thanol™ 4070); hydrocarbon surfactants H-5 (Triton™ X-100, ethoxylated octylphenol) and H-21 (Mapeg™ DO-400, polyethylene glycol dioleate); S-2 (Tegopren™ 5840, polyoxyethylene-functional silicone) and S-3 (Silwet™ L-77, ethoxylated silicone); and blends thereof, were incorporated into Escorene™ 3505 polypropylene at various wt % levels, and nonwoven webs were extruded using the Melt-Blown Extrusion Procedure.

Using the Flux Test procedure, flux test values were measured over a period of four days, with results presented in Table 12.

TABLE 12

| Example | Fluorochemical Surfactant Name | wt % | Non-Fluorochemical Surfactant Name | wt % | % PEO | Flux Test Value After: Day 1 | Day 2 | Day 3 | Day 4 |
|---|---|---|---|---|---|---|---|---|---|
| Combinations of fluorochemical and hydrocarbon surfactants | | | | | | | | | |
| C193 | F-5 | 1.00 | — | — | — | 5 | 12 | 12 | 15 |
| C194 | — | — | H-5 | 2.00 | 67 | 300 | 104 | 230 | 12 |
| 122 | F-5 | 0.50 | H-5 | 0.50 | 67 | 11 | 23 | 52 | 33 |
| 123 | F-5 | 0.75 | H-5 | 0.25 | 67 | 15 | 17 | 21 | 14 |
| C195 | F-8 | 1.00 | — | — | — | 227 | 79 | 96 | 76 |
| C196 | — | — | H-5 | 2.00 | 67 | 300 | 104 | 230 | 12 |
| 124 | F-8 | 0.50 | H-5 | 0.50 | 67 | 33 | 11 | 10 | 6 |
| 125 | F-8 | 0.75 | H-5 | 0.25 | 67 | 6 | 14 | 13 | 9 |
| C197 | F-9 | 1.50 | — | — | — | >300 | N/R | N/R | N/R |
| C198 | — | — | H-5 | 2.00 | 67 | 300 | 104 | 230 | 12 |
| 126 | F-9 | 0.75 | H-5 | 0.75 | 67 | 92 | 2 | 3 | 2 |
| C199 | F-8 | 1.00 | — | — | — | 227 | 79 | 96 | 76 |
| C200 | — | — | H-21 | 1.00 | 42 | 300 | 71 | 31 | 13 |
| 127 | F-8 | 0.50 | H-21 | 0.50 | 42 | 5 | 4 | 3 | 3 |
| Combinations of fluorochemical and silicone surfactants | | | | | | | | | |
| C201 | F-5 | 1.00 | — | — | — | 5 | 12 | 12 | 15 |
| C202 | — | — | S-2 | 1.00 | 43 | 13 | 3 | 22 | 60 |
| 128 | F-5 | 0.50 | S-2 | 0.50 | 43 | 4 | 6 | 35 | 5 |
| C203 | F-5 | 1.00 | — | — | — | 5 | 12 | 12 | 15 |
| C204 | — | — | S-3 | 1.00 | 51 | 14 | 5 | 8 | 24 |
| 129 | F-5 | 0.50 | S-3 | 0.50 | 51 | 52 | 13 | 10 | 6 |

The data in Table 12 show that the combination of a fluorochemical surfactant with either a hydrocarbon or a silicone surfactant incorporated as a melt additive into polypropylene imparted durable hydrophilicity as measured by the Flux Test, with values remaining good after four days of testing.

A synergistic effect on flux test values occurred with the blends of fluorochemical and hydrocarbon surfactants, compared to using each surfactant alone at the same wt %.

During the fourth day of testing, superior flux test values with blends of fluorochemical and silicone surfactants occurred when compared to using either surfactant alone.

Examples 130–137 and Comparative Examples C205–C226

In Examples 130–137 and Comparative Examples C205–C226, fluorochemical surfactant F-5, hydrocarbon surfactant H-5, and blends of F-5 and H-5 were incorporated into polybutylene, polyurethane, polyethylene, polybutylene terephthalate (PBT), nylon and polypropylene thermoplastic polymers, and nonwoven webs were extruded using the Melt-Blown Extrusion Procedure.

The hydrophilicity of each nonwoven web was measured using the Hydrophilicity Test, with results presented in Table 13.

TABLE 13

| Example | Thermoplastic Polymer | F-5 wt % | H-5 wt % | Hydrophilicity Hot | Cold |
|---|---|---|---|---|---|
| C205 | Polybutylene 8510 | — | — | 5 | 5 |
| C206 | Polybutylene 8510 | 2.0 | — | 1 | 1 |
| C207 | Polybutylene 8510 | — | 2.0 | 5 | 5 |
| 130 | Polybutylene 8510 | 1.0 | 1.0 | 1 | 1 |
| C208 | Polybutylene 8510 | 1.0 | — | 1 | 3 |
| C209 | Polybutylene 8510 | — | 1.0 | 5 | 5 |
| 131 | Polybutylene 8510 | 0.5 | 0.5 | 4 | 4 |
| C210 | Polyurethane PS 400 | — | — | 5 | 5 |
| C211 | Polyurethane PS 400 | 1.0 | — | 3 | 3 |
| C212 | Polyurethane PS 400 | — | 1.0 | 3 | 4 |
| 132 | Polyurethane PS 400 | 0.5 | 0.5 | 3 | 3 |
| C213 | Polyethylene 6806 | — | — | 5 | 5 |
| C214 | Polyethylene 6806 | 1.0 | — | 1 | 1 |
| C215 | Polyethylene 6806 | — | 1.0 | 1 | 1 |
| 133 | Polyethylene 6806 | 0.5 | 0.5 | 1 | 1 |
| C216 | Polyethylene 6806 | 0.4 | — | 1 | 4 |
| C217 | Polyethylene 6806 | — | 0.4 | 1 | 2 |
| 134 | Polyethylene 6806 | 0.2 | 0.2 | 1 | 2 |
| C218 | PBT 2002 | — | — | 4 | 5 |
| C219 | PBT 2002 | 1.0 | — | 1 | 3 |
| C220 | PBT 2002 | — | 1.0 | 4 | 5 |
| 135 | PBT 2002 | 0.5 | 0.5 | 3 | 5 |
| C221 | Nylon B-3 | — | — | 3 | 3 |
| C222 | Nylon B-3 | 1.0 | — | 1 | 1 |
| C223 | Nylon B-3 | — | 1.0 | 1 | 1 |
| 136 | Nylon B-3 | 0.5 | 0.5 | 1 | 1 |
| C224 | Polypropylene 3505 | — | — | 5 | 5 |
| C225 | Polypropylene 3505 | 1.0 | — | 2 | 3 |
| C226 | Polypropylene 3505 | — | 1.0 | 4 | 5 |
| 137 | Polypropylene 3505 | 0.5 | 0.5 | 1 | 2 |

The data in Table 13 show that, except for polybutylene terephthalate, the combination of fluorochemical surfactant F-5 and hydrocarbon surfactant H-5 contributed synergism in hydrophilicity to all the thermoplastic polymers.

Examples 138–143 and Comparative Examples C227–C232

In Examples 138–143 and Comparative Examples C227–C232, fluorochemical surfactant F-18, F-20 and F-21, hydrocarbon surfactants H-5 and H-22, and blends thereof, were incorporated into Escorene™ 3445 polypropylene at 1.00 wt % total levels. This time, nonwoven webs were extruded using the Spun-Bond Extrusion Procedure rather than using the Melt-Blown Extrusion Procedure.

The hydrophilicity of each nonwoven web was measured using the Rewet Time Test, Strike Through Test, and Percent Runoff Test. Lower test values in each column indicate greater web hydrophilicity. Test results are presented in Table 14; values given are generally the average of three measurements.

TABLE 14

| Example | Fluorochemical Surfactant | | Non-Fluorochemical Surfactant | | | Rewet Time | Strike Through | Percent Runoff |
|---|---|---|---|---|---|---|---|---|
| | Name | wt % | Name | wt % | % PEO | | | |
| C227 | — | — | — | — | — | 0.10 | 15.38 | 100.00 |
| C228 | F-18 | 1.1 | — | — | — | 0.11 | 2.42 | 14.00 |
| C229 | F-20 | 1.1 | — | — | — | 0.11 | 2.31 | 4.93 |
| C230 | F-21 | 1.1 | — | — | — | 0.10 | 2.28 | 2.4 |
| C231 | — | — | H-5 | 1.1 | 67 | 0.10 | 8.89 | 49.07 |
| C232 | — | — | H-22 | 1.1 | 52 | 0.07 | 14.97 | 76.13 |
| 138 | F-18 | 0.55 | H-5 | 0.55 | 67 | 0.11 | 2.42 | 4.67 |
| 139 | F-18 | 0.55 | H-22 | 0.55 | 52 | 0.09 | 6.30 | 53.73 |
| 140 | F-18 | 0.55 | H-5 | 0.55 | 67 | 0.09 | 2.27 | 0.80 |
| 141 | F-20 | 0.55 | H-5 | 0.55 | 67 | 0.12 | 2.20 | 3.20 |
| 142 | F-20 | 0.55 | H-22 | 0.55 | 52 | 0.22 | 8.93 | 33.33 |
| 143 | F-21 | 0.55 | H-5 | 0.55 | 67 | 0.13 | 3.18 | 0.00 |

The data in Table 14 show that, in a spun-bond propropylene web, bon surfactant H-5 showed synergistic activity with fluorochemical surfactants F-18, F-20 and F-21 in the Strike Through and Runoff Test, giving test values which were lower than expected, indicating higher than expected hydrophilicity.

We claim:

1. A durably hydrophilic, thermoplastic fiber comprising thermoplastic polymer and a mixture of: (a) one or more fluoroaliphatic group-containing nonionic surfactants having one or more polyoxyalkylene groups in their structure, and (b) one or more nonionic, nonfluorinated, polyoxyethylene group-containing surfactants that contain between 20 and 80 weight percent polyoxyethylene, wherein said mixture is present in the fiber at a concentration sufficient to impart durable hydrophilicity to the thermoplastic fiber.

2. The fiber of claim 1 wherein one or more of the nonionic, non-fluorinated, polyoxyethylene group-containing surfactants is according to the formula:

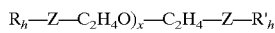

wherein:

$R_h$ is an alkyl or an aryl group, or in combination thereof, that may be substituted or unsubstituted and that contain from 2 to about 20 carbon atoms whose skeletal chain may be straightchained, branched, or, if sufficiently large, cyclic, or any combination thereof, the skeletal chain can optionally include one or more catenary heteroatoms such as oxygen, hexavalent sulfur, and trivalent nitrogen atoms bonded to the carbon atoms of the skeletal chain;

$R'_h$ a hydrogen atom or is an alkyl or an aryl group, or in combination thereof, that may be substituted or unsubstituted and that contain from 2 to about 20 carbon atoms whose skeletal chain may be straight-chained, branched, or, if sufficiently large, cyclic, or any combination thereof, the skeletal chain can optionally include one or more catenary heteroatoms such as oxygen, hexavalent sulfur, and trivalent nitrogen atoms bonded to the carbon atoms of the skeletal chain; one or both of the depicted $R_h$ and $R'_h$ may contain a polydialkylsiloxane group of the formula:

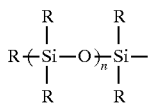

where all the depicted R groups are independently selected as alkyl or aryl groups having from 2 to about 10 carbon atoms that may be substituted or unsubstituted, straight-chained or branched, cyclic or acyclic, and may contain one or more catenary heteroatoms;

Z is an oxygen or sulfur atom or is of the formula —CO—, —COO—, —NH—, —CONH—, or —N(R)— where R is an a substituted or unsubstituted alkyl or aryl group having from 1 to 10 carbon atoms that may contain catenary heteroatoms such as oxygen, sulfur, or nitrogen, and may contain one or more ethylene oxide groups; where R is an alkyl group, that alkyl group may be cyclic or acyclic; and x is a number selected such that the weight percent of polyoxyethylene in the surfactant is between about 20 and 80 percent.

3. The fiber of claim 2 wherein the weight percent of polyoxyethylene in said nonionic, non-fluorinated, polyoxyethylene group-containing surfactant is between 40 and 70 percent.

4. The fiber of claim 2 wherein one or more of the fluoroaliphatic group-containing nonionic surfactants is according to the formula:

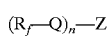

wherein:

$R_f$ is a fluoroaliphatic group having at least 4 fully-fluorinated carbon atoms that may be straight-chained, branched, or, if sufficiently large, cyclic, or any combination thereof, the skeletal chain of which may include one or more catenary heteroatoms bonded only to carbon atoms of the skeletal chain:

Q is a multivalent linking group, or is a covalent bond, that provides a means to link $R_f$ with the depicted group Z, which is a nonionic, water-solubilizing group; Q can comprise a heteroatom-containing group or a combination of such groups;

Z is a nonionic, water-solubilizing group comprising a poly(oxyalkylene) group, $(OR')_x$, where R' is an alkylene group having from 2 to about 4 carbon atoms, and x is a number between about 6 and about 20; and n is a number from 1 to 6.

5. The fiber of claim 2 wherein the thermoplastic polymer is normally hydrophobic and is selected from the group consisting of polyolefin, polyamide, polyester, polyurethane, and blends thereof.

6. The fiber of claim 2 wherein the thermoplastic polymer is polypropylene.

7. The fiber of claim 2 wherein the surfactant mixture is present in up to 2 weight percent based on the weight of the polymer.

8. The fiber of claim 1 wherein one or more of the nonionic, non-fluorinated, polyoxyethylene group-containing surfactants is according to the formula:

$$R-\underset{\underset{(O-CH_2CH_2)_mOR}{|}}{\overset{\overset{R}{|}}{C}}-C\equiv C-\underset{\underset{(O-CH_2CH_2)_nOR}{|}}{\overset{\overset{R}{|}}{C}}-R$$

wherein:

n and m are numbers between 2 and about 20 and are chosen such that the weight percent of polyoxyethylene in the surfactant is between 20 and 80 percent; and each R is selected independently from one another as an alkyl or an aryl group that may be substituted or unsubstituted and that contain from 2 to about 20 carbon atoms whose skeletal chain may be straight-chained, branched, or, if sufficiently large, cyclic, or any combination thereof, such skeletal chain can also optionally include one or more catenary heteroatoms such as oxygen, hexavalent sulfur, and trivalent nitrogen atoms bonded to the carbon atoms of the skeletal chain.

9. The fiber of claim 8 wherein the weight percent of polyoxyethylene in said nonionic, non-fluorinated, polyoxyethylene group-containing surfactant is between 30 and 60 percent.

10. The fiber of claim 8 wherein one or more of the fluoroaliphatic group-containing nonionic surfactants is according to the formula:

$$(R_f-Q)_n-Z$$

wherein:

$R_f$ is a fluoroaliphatic group having at least 4 fully-fluorinated carbon atoms that may be straight-chained, branched, or, if sufficiently large, cyclic, or any combination thereof, the skeletal chain of which may include one or more catenary heteroatoms bonded only to carbon atoms of the skeletal chain;

Q is a multivalent linking group, or is a covalent bond, that provides a means to link $R_f$ with the depicted group Z, which is a nonionic, water-solubilizing group; Q can comprise a heteroatoms-containing group or a combination of such groups;

Z is a nonionic, water-solubilizing group comprising a poly(oxyalkylene) group, $(OR')_x$, where R' is an alkylene group having from 2 to about 4 carbon atoms, and x is a number between about 6 and about 20; and n is a number from 1 to 6.

11. The fiber of claim 8 wherein the thermoplastic polymer is normally hydrophobic and is selected from the group consisting of polyolefin, polyamide, polyester, polyurethane, and blends thereof.

12. The fiber of claim 8 wherein the thermoplastic polymer is polypropylene.

13. The fiber of claim 8 wherein the surfactant mixture is present in up to 2 weight percent based on the weight of the polymer.

14. The fiber of claim 1 wherein one or more of the nonionic, non-fluorinated, polyoxyethylene group-containing surfactants is according to the formula:

$$R-\underset{\underset{R}{|}}{\overset{\overset{R}{|}}{Si}}-O\sim\cdots(Si-O\underset{\underset{R}{|}}{\overset{\overset{R}{|}}{)_x}}\cdots(Si-O\underset{\underset{R}{|}}{\overset{\overset{R}{|}}{)_x}}\cdots\sim\underset{\underset{R}{|}}{\overset{\overset{R}{|}}{Si}}-R$$

$$Q-(CH_2CH_2O)_y\cdots(CH_2CHO)_z-R$$
$$\phantom{Q-(CH_2CH_2O)_y\cdots(}\underset{CH_3}{|}$$

wherein:

n, x, y, and z denote the number of repeating units in the depicted surfactant and are chosen such that the weight percent of polyoxyethylene in the surfactant is between 20 and 80 percent-, Q is a multivalent linking group, or is a covalent bond, that provides a means to link the silicon atom to the depicted oxyalkylene group; Q can comprise a heteroatoms-containing group or a combination of such groups; and each R is selected independently from one another as an alkyl or an aryl group that may be substituted or unsubstituted and that contain from 2 to about 20 carbon atoms whose skeletal chain may be straight-chained, branched, or, if sufficiently large, cyclic, or any combination thereof, the skeletal chain can optionally include one or more catenary heteroatoms such as oxygen, hexavalent sulfur, and trivalent nitrogen atoms bonded to the carbon atoms of the skeletal chain.

15. The fiber of claim 14 wherein the weight percent of polyoxyethylene in said nonionic, non-fluorinated, polyoxyethylene group-containing surfactant is between 40 and 70 percent.

16. The fiber of claim 14 wherein one or more of the fluoroaliphatic group-containing nonionic surfactants is according to the formula:

$$(R_f-Q)_n-Z$$

wherein:

$R_f$ is a fluoroaliphatic group having at least 4 fully-fluorinated carbon atoms that may be straight-chained, branched, or, if sufficiently large, cyclic, or any combination thereof, the skeletal chain of which may include one or more catenary heteroatoms bonded only to carbon atoms of the skeletal chain;

Q is a multivalent linking group, or is a covalent bond, that provides a means to link $R_f$ with the depicted group Z, which is a nonionic, water-solubilizing group; Q can comprise a heteroatoms-containing group or a combination Qf such groups-, Z is a nonionic, water-solubilizing group comprising a poly(oxyalkylene) group, $(OR')_x$, where R' is an alkylene group having from 2 to about 4 carbon atoms, and x is a number between about 6 and about 20; and n is a number from 1 to 6.

17. The fiber of claim 14 wherein the thermoplastic polymer is normally hydrophobic and is selected from the group consisting of polyolefin, polyamide, polyester, polyurethane, and blends thereof.

18. The fiber of claim 14 wherein the thermoplastic polymer is polypropylene.

19. The fiber of claim 14 wherein the surfactant mixture is present in up to 2 weight percent based on the weight of the polymer.

20. A fabric comprising the fiber of claim 1.

21. The fabric of claim 20 wherein the fabric comprises a nonwoven web.

22. The fabric of claim 20 wherein the fabric comprises a melt blown web.

23. The fabric of claim 22 wherein the melt blown web comprises a blown microfiber web.

24. A fabric comprising the fiber of claim 2.

25. A fabric comprising the fiber of claim 8.

26. A fabric comprising the fiber of claim 14.

27. A multi-layer, aqueous liquid absorbent article comprising:

a) an aqueous liquid impervious backing sheet;

b) an aqueous liquid permeable topsheet; and c) an aqueous liquid absorbent layer positioned between said backing sheet; said topsheet comprising a web of durably hydrophilic, thermoplastic polymer and a mixture of (1) one or more fluoroaliphatic group-containing nonionic surfactants having one or more polyoxyalkylene groups in their structure, and (2) one or more nonionic, non-fluorinated, polyoxyethylene group-containing surfactants that contain between 20 and 80 weight percent polyoxyethylene wherein said mixture is present in the thermoplastic polymer at a concentration sufficient to impart durable hydrophilicity to the polymer.

28. The article of claim 27 wherein the weight percent of polyoxyethylene in said nonionic, non-fluorinated, polyoxyethylene group-containing surfactant is between 40 and 70 percent.

29. The article of claim 27 wherein the thermoplastic polymer is normally hydrophobic and is selected from the group consisting of polyolefin, polyamide, polyester, polyurethane, and blends thereof.

30. A film comprising thermoplastic polymer and a mixture of: (a) one or more fluoroaliphatic group-containing nonionic surfactants having one or more polyoxyalkylene groups in their structure, and (b) one or more nonionic, non-fluorinated, polyoxyethylene group-containing surfactants that contain between 20 and 80 weight percent polyxyethylene wherein said mixture is present in the film at a concentration sufficient to impart durable hydrophilicity to the thermoplastic fiber.

31. The film of claim 30 wherein the weight percent of polyoxyethylene in said nonionic, non-fluorinated, polyoxyethylene group-containing surfactant is between 40 and 70 percent.

32. The film of claim 30 wherein the thermoplastic polymer is normally hydrophobic and is selected from the group consisting of polyolefin, polyamide, polyester, polyurethane, and blends thereof.

33. A method of preparing durably hydrophilic fiber or film comprising:

(a) blending thermoplastic polymer with a mixture of: 1) one or more fluoroaliphatic group-containing nonionic surfactants having one or more polyoxyalkylene groups in their structure, and 2) one or more nonionic, nonfluorinated, polyoxyethylene group-containing surfactants that contain between 20 and 80 weight percent polyoxyethylene wherein said mixture is present in the thermoplastic polymer at a concentration sufficient to impart durable hydrophilicity to the polymer;

(b) processing the melt of the blend to produce a fiber or a film with the surfactants dispersed within the fiber or film and present at its surfaces to render those surfaces durably hydrophilic.

34. The method of claim 33 wherein the weight percent of polyoxyethylene in said nonionic, non-fluorinated, polyoxyethylene group-containing surfactant is between 40 and 70 percent.

35. The method of claim 33 wherein the thermoplastic polymer is normally hydrophobic and is selected from the group consisting of polyolefin, polyamide, polyester, polyurethane, and blends thereof.

* * * * *

UNITED STATES PATENT AND TRADEMARK OFFICE
CERTIFICATE OF CORRECTION

PATENT NO.: 5,804,625

DATED: September 8, 1998

INVENTOR(S): John A. Temperante et al.

It is certified that error appears in the above-identified patent and that said Letters Patent is hereby corrected as shown below:

Col. 35, line 51, replace the formula in the printed patent with:

-- $R_h\text{-}Z\text{-}(C_2H_4O)_x\text{-}C_2H_4\text{-}Z\text{-}R'_h$ --.

Col. 38, lines 18-25, replace the formula in the printed patent with:

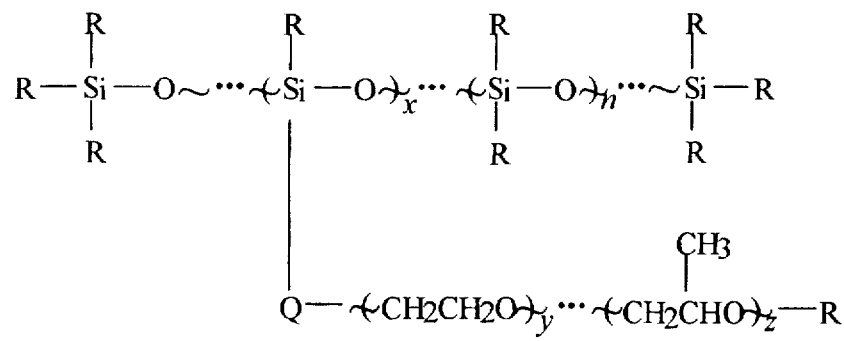

Signed and Sealed this

Twenty-second Day of June, 1999

Q. TODD DICKINSON

Attest:

Attesting Officer

Acting Commissioner of Patents and Trademarks